(12) United States Patent
Miyasaka et al.

(10) Patent No.: US 10,806,968 B2
(45) Date of Patent: Oct. 20, 2020

(54) ELECTRONIC APPARATUS, PROGRAM, METHOD, SYSTEM, AND RECORDING MEDIUM THAT OUTPUT A DIFFERENCE BETWEEN A LEFT AND RIGHT STROKE OF A SWIMMER

(71) Applicant: SEIKO EPSON CORPORATION, Tokyo (JP)

(72) Inventors: Eiji Miyasaka, Okaya (JP); Osamu Yamada, Chino (JP)

(73) Assignee: SEIKO EPSON CORPORATION, Tokyo (JP)

( * ) Notice: Subject to any disclaimer, the term of this patent is extended or adjusted under 35 U.S.C. 154(b) by 400 days.

(21) Appl. No.: 15/783,381

(22) Filed: Oct. 13, 2017

(65) Prior Publication Data
US 2018/0117415 A1 May 3, 2018

(30) Foreign Application Priority Data
Oct. 31, 2016 (JP) .................................. 2016-212759

(51) Int. Cl.
| | |
|---|---|
| A63B 24/00 | (2006.01) |
| G16H 20/30 | (2018.01) |
| G16H 40/67 | (2018.01) |
| G16H 40/63 | (2018.01) |
| G06K 9/00 | (2006.01) |
| G09B 19/00 | (2006.01) |
| A63B 69/12 | (2006.01) |

(52) U.S. Cl.
CPC .......... *A63B 24/0062* (2013.01); *A63B 69/12* (2013.01); *G06K 9/00342* (2013.01); *G06K 9/00355* (2013.01); *G09B 19/0038* (2013.01); *G16H 20/30* (2018.01); *G16H 40/63* (2018.01); *G16H 40/67* (2018.01); *A63B 2024/0071* (2013.01); *A63B 2220/22* (2013.01); *A63B 2220/40* (2013.01); *A63B 2225/50* (2013.01); *A63B 2225/60* (2013.01)

(58) Field of Classification Search
CPC .. G06K 9/00342; G09B 19/003; G16H 40/63; G16H 40/67; G16H 20/30; A63B 24/0062; A63B 69/12; A63B 2024/0071; A63B 2220/22; A63B 2220/40; A63B 2225/50; A63B 2225/60
See application file for complete search history.

(56) References Cited

U.S. PATENT DOCUMENTS

| | | |
|---|---|---|
| 9,168,419 B2 | 10/2015 | Hong et al. |
| 9,251,719 B2 | 2/2016 | Ellis et al. |

(Continued)

FOREIGN PATENT DOCUMENTS

| | | | |
|---|---|---|---|
| JP | 2003-117041 A | 4/2003 | |
| WO | WO 2015/164944 A1 * | 5/2015 | ......... G09B 19/0038 |

OTHER PUBLICATIONS

Thomas Nikodelis."Bilateral inter-arm coordination in freestyle swimming: Effect of skill level and swimming speed"., Journal of Sports Sciences • Jul. 2005 (Year: 2005).*

*Primary Examiner* — Yoshihisa Ishizuka
(74) *Attorney, Agent, or Firm* — Oliff PLC

(57) ABSTRACT

An electronic apparatus includes a processor that outputs information regarding a difference between left and right strokes in swimming on the basis of data which is output from a sensor mounted on the body of a user during swimming.

19 Claims, 16 Drawing Sheets

(56) References Cited

U.S. PATENT DOCUMENTS

2011/0153042 A1* 6/2011 Burton ............... A63B 24/0062
　　　　　　　　　　　　　　　　　　　　700/91
2014/0228649 A1* 8/2014 Rayner ................ A61B 5/1118
　　　　　　　　　　　　　　　　　　　　600/301

* cited by examiner

ELECTRONIC APPARATUS, PROGRAM, METHOD, SYSTEM, AND RECORDING MEDIUM THAT OUTPUT A DIFFERENCE BETWEEN A LEFT AND RIGHT STROKE OF A SWIMMER

CROSS REFERENCE

This application claims priority to Japanese Patent Application No. 2016-212759, filed Oct. 31, 2016, the entire disclosure of which is expressly incorporated herein by reference.

BACKGROUND

1. Technical Field

The present disclosure relates to an electronic apparatus, a program, a method, a system and a recording medium.

2. Related Art

JP-A-2003-117041 discloses an imaging portion imaging a swimmer during swimming and outputting image data every predetermined time, a pixel extracting portion extracting pixels corresponding to an image of the body of the swimmer in each piece of image data, and a portion calculating at least one of the time required for each stroke of the swimmer and an advancing distance based on each stroke on the basis of an advancing direction of the swimmer or a stroke point which is perpendicular to the advancing direction.

However, the method disclosed in JP-A-2003-117041 requires a large-scaled system, and is not appropriate for personal use since a calculation load required for data analysis is also considerable.

The specification of U.S. Pat. No. 9,251,719 discloses a technique in which sensors such as a flowmeter and an accelerometer are mounted on the body of a swimmer, and a total distance, a stroke time, and the like are displayed. If these sensors are used, a large-scaled system is not necessary, and a calculation load required for data analysis is reduced, a measurement function disclosed in the specification of U.S. Pat. No. 9,251,719 can be sufficiently installed in a personal apparatus. However, indexes (a distance, time, and the like) acquired according to the technique disclosed in the specification of U.S. Pat. No. 9,251,719 do not directly reflect the quality of a swimming form, and are thus hardly used by general users such as swimming beginners.

On the other hand, the specification of U.S. Pat. No. 9,168,419 discloses a method of analyzing a stroke cycle in a single swimming stroke by using a plurality of sensors such as a motion sensor, a magnetic sensor, an atmospheric pressure sensor, a GPS, and a temperature sensor.

However, even the stroke cycle acquired according to the technique disclosed in the specification of U.S. Pat. No. 9,168,419 cannot be directly reflected in left-right-balance of a swimming form, and thus there is a problem in that it is not sufficient for general users such as swimming beginners to use the stroke cycle.

SUMMARY

An advantage of some aspects is to provide an electronic apparatus, a program, a system, a method, and a recording medium, suitable for a general user (or swimmer) to easily check the quality of a swimming form of the user.

This can be implemented as the following forms or application examples.

Application Example 1

An electronic apparatus according to this application example includes a processor that outputs information regarding a difference (left-right difference) between left and right strokes in swimming on the basis of data which is output from a sensor mounted on the body of a user during swimming.

Since information output from the processor changes depending on cases where at least left-right-balance of swimming forms of a user is favorable and unfavorable, a user can check the quality of at least the left-right-balance of the swimming forms of the user on the basis of the information. Therefore, the information is effective information suitable for easily checking the swimming forms.

Application Example 2

In the electronic apparatus according to the application example, the processor may output deviation between a curve related to a temporal change in a depth of a right stroke in the swimming and a curve related to a temporal change in a depth of a left stroke in the swimming as at least one of pieces of the information regarding a left-right difference.

Therefore, a user can check the quality of left-right-balance of a swimming form of the user on the basis of deviation between a curve related to a temporal change in a depth of a right stroke in swimming and a curve related to a temporal change in a depth of a left stroke in the swimming.

Application Example 3

In the electronic apparatus according to the application example, the processor may output a difference between the time required for a right stroke in the swimming and the time required for a left stroke in the swimming as at least one of pieces of the information regarding a left-right difference.

Therefore, a user can check the quality of left-right-balance of a swimming form of the user on the basis of a difference between the time required for a right stroke in swimming and the time required for a left stroke in the swimming.

Application Example 4

In the electronic apparatus according to the application example, the processor may output a difference between driving force based on a right stroke in the swimming and driving force based on a left stroke in the swimming as at least one of pieces of the information regarding a left-right difference.

Therefore, a user can check the quality of left-right-balance of a swimming form of the user on the basis of a difference between driving force based on a right stroke in swimming and driving force based on a left stroke in the swimming.

Application Example 5

In the electronic apparatus according to the application example, the processor calculates deviation relative to a predetermined straight advancing direction due to a difference between driving force based on a right stroke in the swimming and driving force based on a left stroke in the swimming, and outputs the extent of the calculated deviation as at least one of pieces of the information regarding a left-right difference.

Therefore, a user can check the quality of left-right-balance of a swimming form of the user on the basis of deviation relative to a predetermined straight advancing direction due to a difference between driving force based on a right stroke in swimming and driving force based on a left stroke in the swimming.

Application Example 6

In the electronic apparatus according to the application example, the processor may output a difference between time for which the body is rolling to the right arm side and time for which the body is rolling to the left arm side, with an advancing direction in the swimming as a rotation axis, as at least one of pieces of the information regarding a left-right difference.

Therefore, a user can check the quality of left-right-balance of a swimming form of the user on the basis of a difference between time for which the body is rolling to the right arm side and time for which the body is rolling to the left arm side, with an advancing direction in swimming as a rotation axis.

Application Example 7

An electronic apparatus according to this application example includes a display that displays information regarding a difference (left-right difference) between left and right strokes in swimming on the basis of data which is output from a sensor mounted on the body of a user during swimming.

Since information displayed on the display changes depending on cases where at least left-right-balance of swimming forms of a user is favorable and unfavorable, a user can check the quality of at least the left-right-balance of the swimming forms of the user on the basis of the information. Therefore, the information is effective information suitable for easily checking the swimming forms.

Application Example 8

In the electronic apparatus according to the application example, the information regarding a left-right difference may include a graph in which a curve related to a temporal change in a depth of a right stroke in the swimming overlaps a curve related to a temporal change in a depth of a left stroke in the swimming.

Therefore, a user can check the quality of left-right-balance of a swimming form of the user on the basis of deviation, expressed by a graph, between a curve related to a temporal change in a depth of a right stroke in swimming and a curve related to a temporal change in a depth of a left stroke in the swimming.

Application Example 9

In the electronic apparatus according to the application example, the information regarding a left-right difference may include a graph indicating a difference between the time required for a right stroke in the swimming and the time required for a left stroke in the swimming.

Therefore, a user can check the quality of left-right-balance of a swimming form of the user on the basis of a difference, expressed by a graph, between the time required for a right stroke in swimming and the time required for a left stroke in the swimming.

Application Example 10

In the electronic apparatus according to the application example, the information regarding a left-right difference may include a graph indicating a difference between driving force based on a right stroke in the swimming and driving force based on a left stroke in the swimming.

Therefore, a user can check the quality of left-right-balance of a swimming form of the user on the basis of a difference, expressed by a graph, between driving force based on a right stroke in swimming and driving force based on a left stroke in the swimming.

Application Example 11

In the electronic apparatus according to the application example, the information regarding a left-right difference may include a graph indicating deviation relative to a predetermined straight advancing direction due to a difference between driving force based on a right stroke in the swimming and driving force based on a left stroke in the swimming.

Therefore, a user can check the quality of left-right-balance of a swimming form of the user on the basis of deviation relative to a predetermined straight advancing direction, expressed by a graph, due to a difference between driving force based on a right stroke in swimming and driving force based on a left stroke in the swimming.

Application Example 12

In the electronic apparatus according to the application example, the information regarding a left-right difference may include a graph indicating a difference between time for which the body is rolling to the right arm side and time for which the body is rolling to the left arm side, with an advancing direction in the swimming as a rotation axis.

Therefore, a user can check the quality of left-right-balance of a swimming form of the user on the basis of a difference, expressed by a graph, between time for which the body is rolling to the right arm side and time for which the body is rolling to the left arm side, with an advancing direction in the swimming as a rotation axis.

Application Example 13

In the electronic apparatus according to the application example, the sensor may include at least one of an atmospheric pressure sensor, an acceleration sensor, and an angular velocity sensor.

A curve related to a temporal change in a depth of a stroke may be generated on the basis of, for example, an output from the atmospheric pressure sensor; the time required for a stroke may be generated on the basis of, for example, at least one of outputs from the atmospheric pressure sensor, the acceleration sensor, and the angular velocity sensor; and driving force may be generated on the basis of, for example, at least one of outputs from the acceleration sensor and the angular velocity sensor.

Application Example 14

A program according to this application example causes a computer to execute a process of outputting or displaying information regarding a difference between left and right strokes in swimming on the basis of data which is output from a sensor mounted on the body of a user during swimming.

Since information output or displayed by the computer changes depending on cases where at least left-right-balance of swimming forms of a user is favorable and unfavorable, a user can check the quality of at least the left-right-balance of the swimming forms of the user on the basis of the information. Therefore, the information is effective information suitable for easily checking the swimming forms.

Application Example 15

A control method according to this application example includes performing control so that information regarding a difference between left and right strokes in swimming is output or displayed on the basis of data which is output from a sensor mounted on the body of a user during swimming.

Since information output or displayed by the computer changes depending on cases where at least left-right-balance of swimming forms of a user is favorable and unfavorable, a user can check the quality of at least the left-right-balance of the swimming forms of the user on the basis of the information. Therefore, the information is effective information suitable for easily checking the swimming forms.

Application Example 16

A computer readable recording medium according to this application example records a program causing a computer to execute a process of outputting or displaying information regarding a difference between left and right strokes in swimming on the basis of data which is output from a sensor mounted on the body of a user during swimming.

Since information output or displayed by the computer changes depending on cases where at least left-right-balance of swimming forms of a user is favorable and unfavorable, a user can check the quality of at least the left-right-balance of the swimming forms of the user on the basis of the information. Therefore, the information is effective information suitable for easily checking the swimming forms.

Application Example 17

A system according to this application example includes any one of the electronic apparatuses; and a sensor.

Application Example 18

In the electronic apparatus according to the application example, the information may include advice.

Application Example 19

In the electronic apparatus according to the application example, the processor may output a curve related to a temporal change in a depth of a stroke in the swimming and a curve related to a temporal change in a depth of a stroke in the swimming of another user who is different from the user in an overlapping manner.

Such a curve can be used to improve a form of a user.

Application Example 20

In the electronic apparatus according to the application example, the processor may determine a swimming stroke on the basis of a curve related to a temporal change in a depth of the stroke in the swimming, and may output the determined result.

Since the output information is correlated with a swimming stroke, a user can look back on the swimming stroke by using the information as a practice diary, and thus the information can be used to improve a swimming form of the user.

BRIEF DESCRIPTION OF THE DRAWINGS

Embodiments will be described with reference to the accompanying drawings, wherein like numbers reference like elements.

DESCRIPTION OF EXEMPLARY EMBODIMENTS

The embodiments described below are not intended to improperly limit the content of the invention disclosed in the appended claims. In addition, all constituent elements described below are not essential constituent elements of the invention.

1. System 1-1. Summary of System

Figure 1:
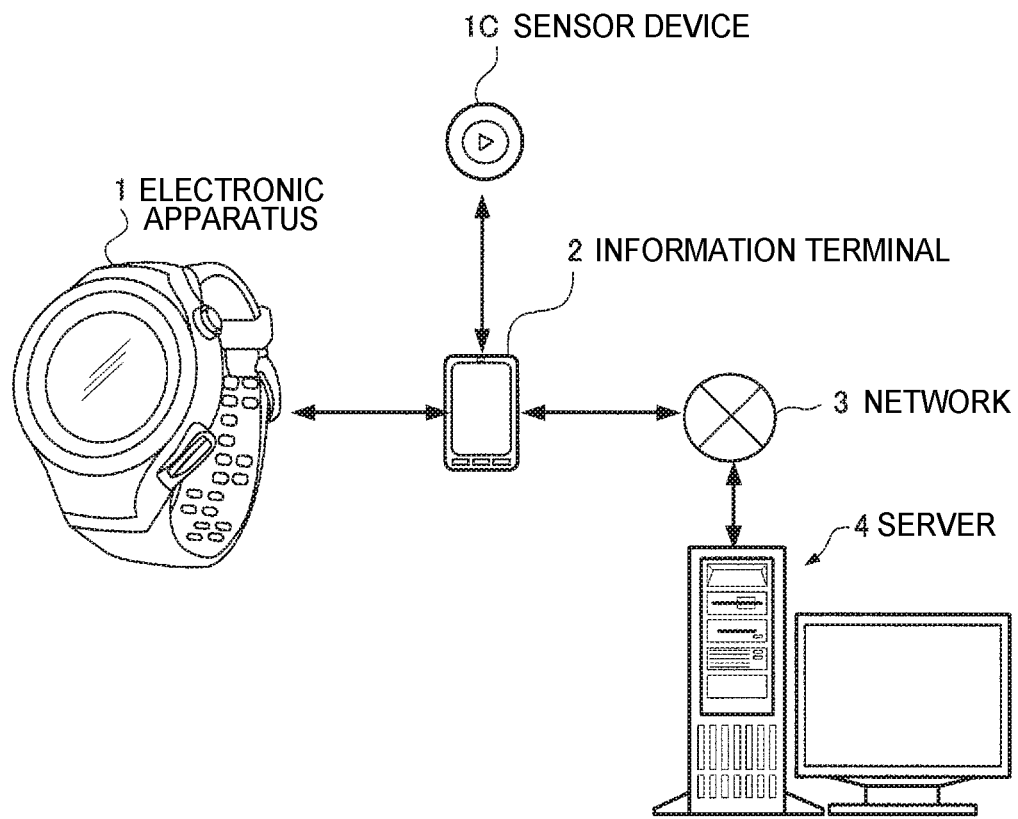
FIG. 1 illustrates an example of a diagram for explaining a summary of a system.

As illustrated in FIG. 1, a system of the present embodiment includes an electronic apparatus 1, a sensor device 1C, an information terminal 2, and a server 4. Each of the information terminal 2 and the server 4 is connectable to a network 3 such as the Internet, and the information terminal 2 and the server 4 can perform communication with each other via the network 3. The electronic apparatus 1 can perform communication with the information terminal 2 via short-range radio communication or the like. The sensor device 1C can perform communication with the information terminal 2 via short-range radio communication or the like. The electronic apparatus 1 and the sensor device 1C may directly communicate with each other via short-range radio communication or the like (a user may use the electronic apparatus 1 as a master device, and may use the sensor device 1C as a slave device). In the system of the present embodiment, some of the electronic apparatus 1, the sensor device 1C, the information terminal 2, and the server 4 may be omitted.

Each of the electronic apparatus 1 and the sensor device 1C is, for example, a waterproof type apparatus on which various sensors are mounted, and acquires measured data during swimming by driving at least one sensor. At least one of the electronic apparatus 1 and the sensor device 1C is mounted a user's body during swimming. The "swimming" mentioned here includes all swims such as a swim in triathlon and a swimming race, and a location where swimming is performed is any one of, for example, a sea, a lake, a river, and an indoor pool.

A mounting location of the electronic apparatus 1 is, for example, a part (forearm) from the elbow to the hand. The electronic apparatus 1 is formed of a wrist type (wristwatch type) electronic apparatus (outdoor watch) so that measured data regarding a user's living body can be acquired in a contact or noncontact manner, or the user can view the electronic apparatus 1 or the sensor device 1C when necessary, and a mounting location of the electronic apparatus 1 is the wrist of the user. A mounting tool (belt) suitable for a shape of the wrist is used when the electronic apparatus 1 is mounted on the wrist.

A mounting location of the sensor device 1C may be appropriately selected by the user according to a swimming stroke, measurement purpose, or the like. A mounting location of the sensor device 1C is, for example, any one of the user's head, neck, upper arm, front arm, waist, chest, thigh, crus, and ankle. Here, it is assumed that the number of sensor device 1C is one, but may be two or more. In this case, for example, the two sensor devices 1C may be separately mounted on the right wrist and the left wrist of the user. When the sensor device 1C is mounted on a part of the body, a mounting tool (a belt or a clip) suitable for a shape of the part or a shape of a swimwear may be used.

The information terminal 2 is an information terminal used by the user of the electronic apparatus 1 or the sensor device 1C, and is formed of, for example, a smartphone, a portable or desktop personal computer (PC) or a tablet PC. The information terminal 2 is used for the user to perform settings on the electronic apparatus 1 or the sensor device 1C, for example, before swimming. The information terminal 2 is used for the user to read measured data regarding the user from the electronic apparatus 1 or the sensor device 1C, for example, after swimming, or to upload the read measured data to the server 4.

The server 4 provides information related to use of the electronic apparatus 1 to a user of the electronic apparatus 1, or manages measured data acquired by the electronic apparatus 1 or the sensor device 1C for each user. The information provided by the server 4 includes at least one of a program for operating the information terminal 2, a program for operating the electronic apparatus 1, and a program for operating the sensor device 1C.

1-2. Configuration of System 1-2-1. Configuration of Sensor Device

Figure 2:
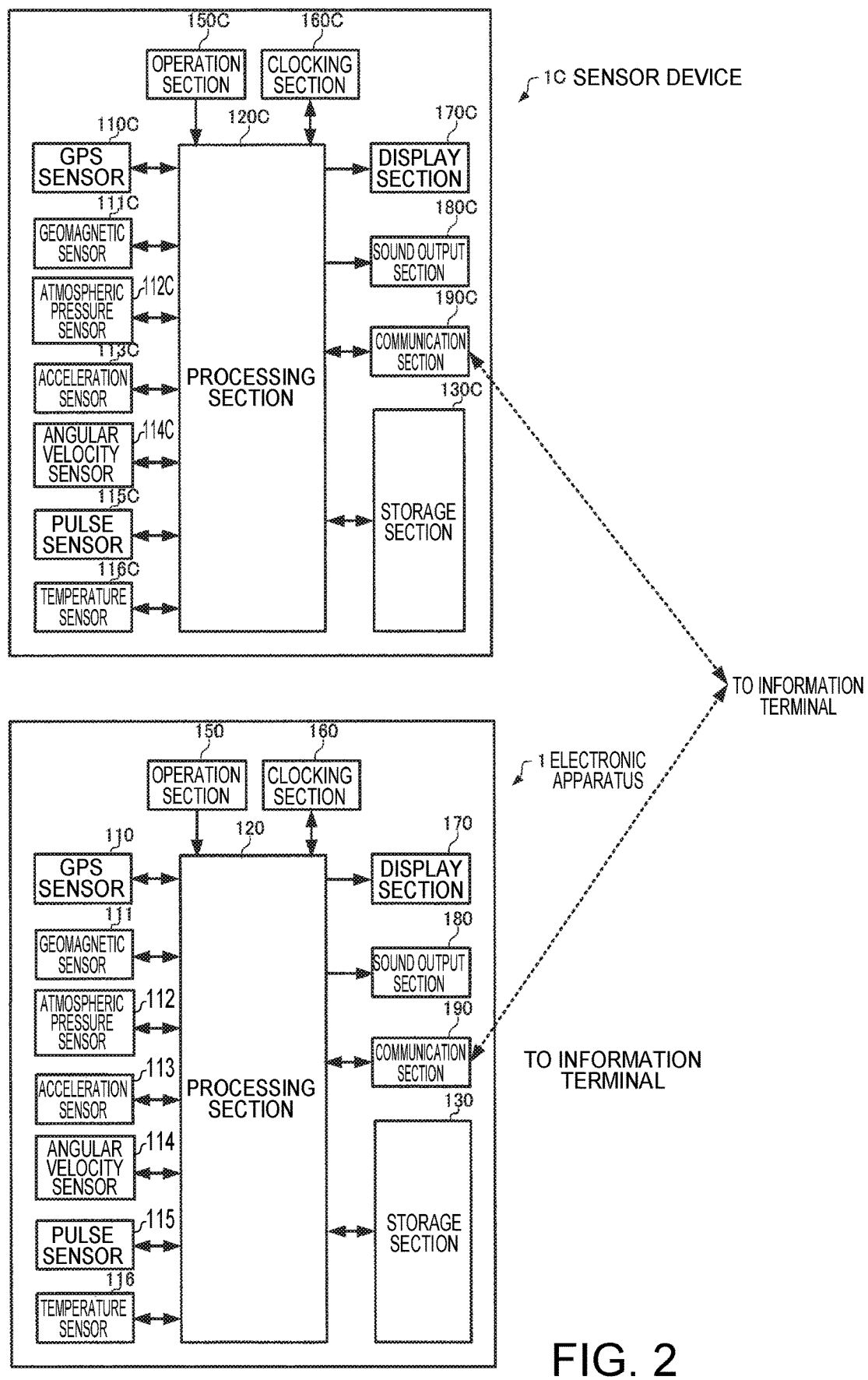
FIG. 2 illustrates an example of a functional block diagram of a sensor device and an electronic apparatus.

As illustrated in FIG. 2, the sensor device 1C is configured to include a GPS sensor 110C, a geomagnetic sensor 111C, an atmospheric pressure sensor 112C, an acceleration sensor 113C, an angular velocity sensor 114C, a pulse sensor 115C, a temperature sensor 116C, a processor 120C, a storage section 130C, an operation section 150C, a clocking section 160C, a display 170C, a sound output section 180C, a communicator 190C, and the like. However, a configuration of the sensor device 1C may have a configuration in which some of the constituent elements are deleted or changed, or may have a configuration in which other constituent elements (for example, a humidity sensor and an ultraviolet sensor) are added thereto.

The GPS sensor 110C is a sensor which generates positioning data (data such as latitude, longitude, altitude and velocity vector) indicating a position and the like of the sensor device 1C and outputs the data to the processor 120C, and is formed of, for example, a global positioning system (GPS) receiver. The GPS sensor 110C receives an electromagnetic wave with a predetermined frequency bandwidth incoming from the outside by using a GPS antenna (not illustrated), extracts a GPS signal sent from a GPS satellite therefrom, and also generates positioning data indicating a position or the like of the sensor device 1C on the basis of the GPS signal.

The geomagnetic sensor 111C is a sensor which detects a geomagnetic vector indicating a direction of a magnetic field of the earth, viewed from the sensor device 1C, and generates, for example, geomagnetic data indicating magnetic flux densities in three-axis directions which are orthogonal to each other. For example, a magnet resistive (MR) element, a magnet impedance (MI) element, or a hole element is used for the geomagnetic sensor 111C.

The atmospheric pressure sensor 112C is a sensor which detects an ambient atmospheric pressure (atmospheric pressure), and includes, for example, a pressure sensitive element of a type (vibration type) using a change in a resonance frequency of a vibrator element. The pressure sensitive element is a piezoelectric vibrator made of a piezoelectric material such as quartz crystal, Lithium Niobate, or Lithium Tantalate, and employs, for example, a tuning fork type vibrator, a dual-tuning fork type vibrator, an AT vibrator (thickness shear vibrator), or a surface acoustic wave (SAW) vibrator. Alternatively, the atmospheric pressure sensor 112C may be a MEMS type atmospheric pressure sensor manufactured by using a semiconductor manufacturing technique. For example, the atmospheric pressure sensor 112C includes a diaphragm portion which is bent and deformed by received pressure, and a distortion detection element which detects bending of the diaphragm portion. The diaphragm portion is made of, for example, silicon. The distortion detection element is, for example, a piezoelectric resistive element. An output from the atmospheric pressure sensor 112C may be used to correct positioning data.

The acceleration sensor 113C is an inertial sensor which detects respective accelerations in the three-axis directions which intersect (are ideally orthogonal to) each other, and outputs digital signals (acceleration data) corresponding to magnitudes and directions of the detected three-axis accelerations. The outputs from the acceleration sensor 113C may be used to correct position information included in the positioning data from the GPS sensor 110C.

The angular velocity sensor 114C is an inertial sensor which detects respective angular velocities in the three-axis directions which intersect (are ideally orthogonal to) each other, and outputs digital signals (angular velocity data) corresponding to magnitudes and directions of the measured three-axis angular velocities. The outputs from the angular velocity sensor 114C may be used to correct position information included in the positioning data from the GPS sensor 110C.

The pulse sensor 115C is a sensor which generates a signal indicating a pulse of the user and outputs the signal to the processor 120C, and includes, for example, alight source such as an LED light source which applies measurement light having an appropriate wavelength toward a blood vessel under the skin, and a light receiving element which detects a change in the intensity of light generated at the blood vessel according to the measurement light.

The temperature sensor 116C is a temperature sensitive element which outputs a signal (for example, a voltage corresponding to a temperature) corresponding to an ambient temperature. The temperature sensor 116C may output a digital signal corresponding to a temperature.

The storage section 130C is formed of, for example, various integrated circuit (IC) memories such as a read only memory (ROM), a flash ROM, and a random access memory (RAM), or a computer readable recording medium such as a hard disk or a memory card. The storage section 130C is formed of, for example, one or a plurality of IC memories, and includes a ROM storing data such as a program (non-transitory storage medium containing program instructions), and a RAM serving as a work region of the processor 120C. The RAM may include a nonvolatile RAM.

The operation section 150C is formed of, for example, a button, a key, a microphone, and a touch panel so as to have a voice recognition function (using the microphone (not illustrated)) and an action detection function (using the acceleration sensor 113C or the like), and performs a process of converting an instruction from a user into an appropriate signal which is then sent to the processor 120C.

The clocking section 160C is formed of, for example, a real time clock (RTC) IC or the like, and generates time data such as year, month, day, hour, minute, and second, and sends the data to the processor 120C.

The display 170C is formed of, for example, a liquid crystal display (LCD), an organic electroluminescence (EL) display, an electrophoretic display (EPD), or a touch panel display, and displays various images in response to instructions from the processor 120C.

The sound output section 180C is formed of, for example, a speaker, a buzzer, or a vibrator, and generates various sounds (or vibration) in response to instructions from the processor 120C.

The communicator 190C performs a variety of control for establishing data communication between the sensor device 1C and the information terminal 2 (or the smartphone). The communicator 190C is configured to include a transceiver based on a short-range wireless communication standard such as Bluetooth (registered trademark) (including Bluetooth Low Energy (BTLE)), Wi-Fi (registered trademark) (Wireless Fidelity), Zigbee (registered trademark), near field communication (NFC), or ANT+ (registered trademark).

The processor 120C is formed of, for example, a micro processing unit (MPU), a digital signal processor (DSP), and an application specific integrated circuit (ASIC). The processor 120C performs various processes according to a program stored in the storage section 130C (non-transitory storage medium containing program instructions), and various commands which are input by the user via the operation section 150C. The processes in the processor 120C include, for example, data processing on data which is generated by the GPS sensor 110C, the geomagnetic sensor 111C, the atmospheric pressure sensor 112C, the acceleration sensor 113C, the angular velocity sensor 114C, the pulse sensor 115C, the temperature sensor 116C, the clocking section 160C, and the like, display processing for displaying an image on the display 170C, sound output processing for outputting sounds from the sound output section 180C. The processor 120C performs a process of receiving a control command from the information terminal 2 via the communicator 190C, or various computation processes on data which is received from the information terminal 2 via the communicator 190C, according to various programs. The processor 120C performs a process of reading data from the storage section 130C, and transmitting the data to the electronic apparatus 1 in a predetermined format via the communicator 190C, according to various programs. The processor 120C performs a process of transmitting various pieces of information to the information terminal 2 via the communicator 190C, and displaying various screens on the basis of information received from the information terminal 2, according to various programs. The processor 120C performs other various control processes. For example, the processor 120C performs a process of displaying images (images, moving images, text, symbols, and the like) on the display 170C on the basis of at least some of the information received by the communicator 190C, and information stored in the storage section 130C. A vibration mechanism may be provided in the sensor device 1C, and various pieces of information may be converted into vibration information by the vibration mechanism so as to be presented to the user.

1-2-2. Configuration of Electronic Apparatus

As illustrated in FIG. 2, the electronic apparatus 1 is configured to include a GPS sensor 110, a geomagnetic sensor 111, an atmospheric pressure sensor 112, an acceleration sensor 113, an angular velocity sensor 114, a pulse sensor 115, a temperature sensor 116, a processor 120, a storage section 130, an operation section 150, a clocking section 160, a display 170, a sound output section 180, a communicator 190, and the like. However, the electronic apparatus 1 may have a configuration in which some of the constituent elements are deleted or changed, or may have a configuration in which other constituent elements (for example, a humidity sensor and an ultraviolet sensor) are added thereto.

The GPS sensor 110 is a sensor which generates positioning data indicating a position and the like of the electronic apparatus 1 and outputs the data to the processor 120, and is formed of, for example, a global positioning system (GPS) receiver. The GPS sensor 110 receives an electromagnetic wave with a predetermined frequency bandwidth incoming from the outside by using a GPS antenna (not illustrated), extracts a GPS signal sent from a GPS satellite therefrom, and also generates positioning data indicating a position or the like of the electronic apparatus 1 on the basis of the GPS signal.

The geomagnetic sensor 111 is a sensor which detects a geomagnetic vector indicating a direction of a magnetic field of the earth, viewed from the electronic apparatus 1, and generates, for example, geomagnetic data indicating magnetic flux densities in three-axis directions which are orthogonal to each other. For example, a magnet resistive (MR) element, a magnet impedance (MI) element, or a hole element is used for the geomagnetic sensor 111.

The atmospheric pressure sensor 112 is a sensor which detects an ambient atmospheric pressure (atmospheric pressure), and includes, for example, a pressure sensitive element of a type (vibration type) using a change in a resonance frequency of a vibrator element. The pressure sensitive element is a piezoelectric vibrator made of a piezoelectric material such as quartz crystal, Lithium Niobate, or Lithium Tantalate, and employs, for example, a tuning fork type vibrator, a dual-tuning fork type vibrator, an AT vibrator (thickness shear vibrator), or a surface acoustic wave (SAW) vibrator. An output from the atmospheric pressure sensor 112 may be used to correct positioning data.

The acceleration sensor 113 is an inertial sensor which detects respective accelerations in the three-axis directions which intersect (are ideally orthogonal to) each other, and outputs digital signals (acceleration data) corresponding to magnitudes and directions of the measured three-axis accelerations. The outputs from the acceleration sensor 113 may be used to correct position information included in the positioning data from the GPS sensor 110.

The angular velocity sensor 114 is an inertial sensor which detects respective angular velocities in the three-axis directions which intersect (are ideally orthogonal to) each other, and outputs digital signals (angular velocity data) corresponding to magnitudes and directions of the measured three-axis angular velocities. The outputs from the angular velocity sensor 114 may be used to correct position information included in the positioning data from the GPS sensor 110.

The pulse sensor 115 is a sensor which generates a signal indicating a pulse of the user and outputs the signal to the processor 120, and includes, for example, a light source such as a light emitting diode (LED) light source which applies measurement light having an appropriate wavelength toward a blood vessel under the skin, and a light receiving element which detects a change in the intensity of light generated at the blood vessel according to the measurement light.

The temperature sensor 116 is a temperature sensitive element which outputs a signal (for example, a voltage corresponding to a temperature) corresponding to an ambient temperature. The temperature sensor 116 may output a digital signal corresponding to a temperature.

The storage section 130 is formed of, for example, various integrated circuit (IC) memories such as a read only memory (ROM), a flash ROM, and a random access memory (RAM), or a computer readable recording medium such as a hard disk or a memory card. The storage section 130 (non-transitory storage medium containing program instructions) is formed of, for example, one or a plurality of IC memories, and includes a ROM storing data such as a program, and a RAM serving as a work region of the processor 120. The RAM may include a nonvolatile RAM.

The operation section 150 is formed of, for example, a button, a key, a microphone, and a touch panel so as to have a voice recognition function (using the microphone (not illustrated)) and an action detection function (using the acceleration sensor 113 or the like), and performs a process of converting an instruction from the user into an appropriate signal which is then sent to the processor 120.

The clocking section 160 is formed of, for example, a real time clock (RTC) IC or the like, and generates time data such as year, month, day, hour, minute, and second, and sends the data to the processor 120.

The display 170 is formed of, for example, a liquid crystal display (LCD), an organic electroluminescence (EL) display, an electrophoretic display (EPD), or a touch panel display, and displays various images in response to instructions from the processor 120.

The sound output section 180 is formed of, for example, a speaker, a buzzer, or a vibrator, and generates various sounds (or vibration) in response to instructions from the processor 120.

The communicator 190 performs a variety of control for establishing data communication between the electronic apparatus 1 and the information terminal 2 (a smartphone). The communicator 190 is configured to include a transceiver based on a short-range wireless communication standard such as Bluetooth (registered trademark) (including Bluetooth Low Energy (BTLE)), Wi-Fi (registered trademark) (Wireless Fidelity), Zigbee (registered trademark), near field communication (NFC), or ANT+ (registered trademark).

The processor 120 is formed of, for example, a micro processing unit (MPU), a digital signal processor (DSP), and an application specific integrated circuit (ASIC). The processor 120 performs various processes according to a program stored in the storage section 130, and various commands which are input by the user via the operation section 150. The processes in the processor 120 include, for example, data processing on data which is generated by the GPS sensor 110, the geomagnetic sensor 111, the atmospheric pressure sensor 112, the acceleration sensor 113, the angular velocity sensor 114, the pulse sensor 115, the temperature sensor 116, the clocking section 160, and the like, display processing for displaying an image on the display 170, sound output processing for outputting sounds from the sound output section 180. The processor 120 performs a process of receiving a control command from the information terminal 2 via the communicator 190, or various computation processes on data which is received from the information terminal 2 via the communicator 190, according to various programs. The processor 120 performs a process of reading data from the storage section 130, and transmitting the data to the information terminal 2 in a predetermined format via the communicator 190, according to various programs. The processor 120 performs a process of transmitting various pieces of information to the information terminal 2 via the communicator 190, and displaying various screens on the basis of information received from the information terminal 2, according to various programs. The processor 120 performs other various control processes. For example, the processor 120 performs a process of displaying images (images, moving images, text, symbols, and the like) on the display 170 on the basis of at least some of the information received by the communicator 190, and information stored in the storage section 130. A vibration mechanism may be provided in the electronic apparatus 1, and various pieces of information may be converted into vibration information by the vibration mechanism so as to be presented to the user.

1-2-3. Configuration of Information Terminal

Figure 3:
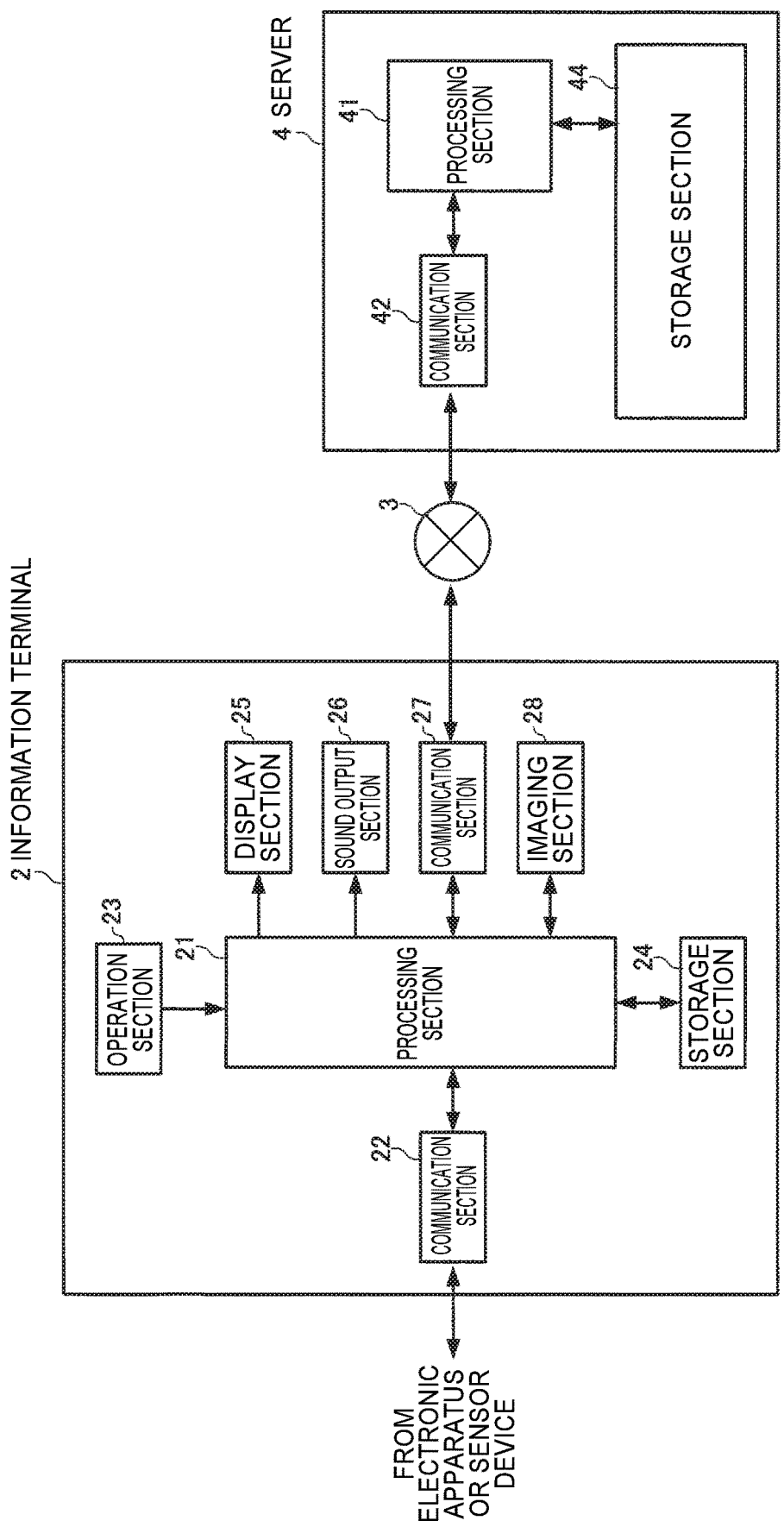
FIG. 3 illustrates an example of a functional block diagram of an information terminal and a server.

As illustrated in FIG. 3, the information terminal 2 is configured to include a processor 21, a communicator 22, an operation section 23, a storage section 24, a display 25, a sound output section 26, a communicator 27, and an imaging section 28. However, the information terminal 2 may have a configuration in which some of the constituent elements are deleted or changed as appropriate, or may have a configuration in which other constituent elements are added thereto.

The communicator 22 performs a process of receiving data (measured data) or the like transmitted from the electronic apparatus 1 or the sensor device 1C in a predetermined format and sending the data to the processor 21, a process of transmitting a control command from the processor 21 to the electronic apparatus 1 or the sensor device 1C, or the like.

The operation section 23 performs a process of acquiring data corresponding to the user's operation, and sending the data to the processor 21. The operation section 23 may be, for example, a touch panel display, a button, a key, and a microphone.

The storage section 24 is formed of, for example, various integrated circuit (IC) memories such as a read only memory (ROM), a flash ROM, and a random access memory (RAM), or a computer readable recording medium such as a hard disk or a memory card. The storage section 24 stores programs for the processor 21 performing various computation processes or control processes, various programs or data for realizing application functions. The storage section 24 is used as a work region of the processor 21, and temporarily stores data which is acquired from the operation section 23, results of calculation executed by the processor 21 according to various programs, and the like. The storage section 24 may store data which is required to be preserved for a long period of time among data items generated through processing in the processor 21.

The display 25 displays a processing result in the processor 21 as text, a graph, a table, animation, and other images. The display 25 may be, for example, a cathode ray tube (CRT), a liquid crystal display (LCD), a touch panel display, and a head mounted display (HMD). A single touch panel display may realize functions of the operation section 23 and the display 25.

The sound output section 26 outputs a processing result in the processor 21 as a sound such as a voice or a buzzer sound. The sound output section 26 may be, for example, a speaker or a buzzer.

The communicator 27 performs data communication with a communicator 42 of the server 4 via the network 3. For example, the communicator 27 performs a process of receiving data from the processor 21 and transmitting the data to the communicator 42 of the server 4 in a predetermined format. For example, the communicator 27 performs a process of receiving information required to display a screen from the communicator 42 of the server 4 and sending the information to the processor 21, or a process of receiving various pieces of information from the processor 21 and transmitting the information to the communicator 42 of the server 4.

The imaging section 28 is a camera including a lens, a color imaging element, a focus adjustment mechanism, and the like, and generates a picture of a field generated by the lens as an image with the imaging element. Data (image data) regarding the image acquired by the imaging element is sent to the processor 21 so as to be preserved in the storage section 24 or displayed on the display 25.

The processor 21 (an example of a computer) is formed of, for example, a central processing unit (CPU), a digital signal processor (DSP), and an application specific integrated circuit (ASIC). The processor 21 performs various processes according to a program stored in the storage section 24, and various commands which are input by the user via the operation section 23. The processes in the processor 21 include, for example, data processing on data which is generated by the electronic apparatus 1 or the sensor device 1C, display processing for displaying an image on the display 25, sound output processing for outputting sounds from the sound output section 26, and image processing on an image acquired by the imaging section 28. The processor 21 may be formed of a single processor, and may be formed of a plurality of processors. The processor 21 performs a process of transmitting a control command to the electronic apparatus 1 via the communicator 22, or various computation processes on data which is received from the electronic apparatus 1 via the communicator 22, according to various programs. The processor 21 performs a process of reading data from the storage section 24, and transmitting the data to the server 4 in a predetermined format via the communicator 27, according to various programs. The processor 21 performs a process of transmitting various pieces of information to the server 4 via the communicator 27, and displaying various screens on the basis of information received from the server 4, according to various programs. The processor 21 performs other various control processes. For example, the processor 21 performs a process of displaying images (images, moving images, text, symbols, and the like) on the display 25 on the basis of at least some of the information received by the communicator 27, the information received by the communicator 22, and information stored in the storage section 24. A vibration mechanism may be provided in the information terminal 2, the electronic apparatus 1, or the sensor device 1C, and various pieces of information may be converted into vibration information by the vibration mechanism so as to be presented to the user.

1-2-4. Configuration of Server

As illustrated in FIG. 3, the server 4 is configured to include a processor 41, a communicator 42, and a storage section 44. However, the server 4 may have a configuration in which some of the constituent elements are deleted or changed as appropriate, or may have a configuration in which other constituent elements are added thereto.

The storage section 44 is formed of, for example, various integrated circuit (IC) memories such as a read only memory (ROM), a flash ROM, and a random access memory (RAM), or a computer readable recording medium such as a hard disk or a memory card. The storage section 44 stores a program for the processor 41 performing various calculation processes or a control process, or various programs or data for realizing application functions. The storage section 44 is used as a work region of the processor 41, and temporarily stores results of calculation executed by the processor 41 according to various programs, and the like. The storage section 44 may store data which is required to be preserved for a long period of time among pieces of data generated through processing of the processor 41. Various pieces of information stored in the storage section 44 will be described later.

The communicator 42 performs data communication with the communicator 27 of the information terminal 2 via the network 3. For example, the communicator 42 performs a process of receiving data from the communicator 27 of the information terminal 2, and sending the data to the processor 41. For example, the communicator 42 performs a process of transmitting information required to display a screen to the communicator 27 of the information terminal 2 in a predetermined format, or a process of receiving information from the communicator 27 of the information terminal 2 and sending the information to the processor 41.

The processor 41 performs a process of receiving data from the information terminal 2 via the communicator 42 and storing the data in the storage section 44, according to various programs. The processor 41 performs a process of receiving various pieces of information from the information terminal 2 via the communicator 42, and transmitting information required to display various screens to the information terminal 2, according to various programs. The processor 41 performs other various control processes.

1-3. Description of Left-Right-Balance Display Process
1-3-1. Left-Right-Balance Display Process Using Arm Atmospheric Pressure Sensor (First Example)

The processor 120 of the electronic apparatus 1 outputs information regarding a difference between left and right strokes (also easily referred to as a left-right difference) in swimming on the basis of data output from a sensor mounted on a user's body during swimming, and the display 170 of the electronic apparatus 1 displays the information regarding a left-right difference.

Hereinafter, details thereof will be described. Herein, a case is assumed in which the single electronic apparatus 1 is sequentially used for measurement related to the right arm and for measurement related to the left arm, and the electronic apparatus 1 performs all of measurement, analysis, and display.

However, in the present system, a single sensor device 1C may be used instead of the electronic apparatus 1. One of the electronic apparatus 1 and the sensor device 1C may be used for measurement related to the right arm, and the other thereof may be used for measurement related to the left arm. Two electronic apparatuses 1 may be prepared, and one of the two electronic apparatuses 1 may be used for measurement related to the right arm, and the other thereof may be used for measurement related to the left arm. Two sensor devices 1C may be prepared, and one of the two sensor devices 1C may be used for measurement related to the right arm, and the other thereof may be used for measurement related to the left arm.

Meanwhile, in the present embodiment, the atmospheric pressure sensor 112 is mounted on the electronic apparatus 1 used for both of measurement related to the right arm and measurement related to the left arm. In a measurement period, the atmospheric pressure sensor 112 outputs sensing data (atmospheric pressure data) corresponding to surrounding atmospheric pressure when the electronic apparatus 1 is in the air, and outputs data (water pressure data) corresponding to surrounding water pressure when the electronic apparatus 1 is under water. In the following description, water pressure data and atmospheric pressure data will be referred to as "atmospheric pressure data" without being differentiated from each other. Since atmospheric pressure data which is output when the atmospheric pressure sensor 112 is under water has a value greater than that of atmospheric pressure data which is output when the atmospheric pressure sensor 112 is in the air, it may be possible to detect whether or not the electronic apparatus 1 is under water on the basis of an output from the atmospheric pressure sensor 112 mounted on the electronic apparatus 1.

1-3-1-1. Right Measurement (First Example)

First, the user mounts the electronic apparatus 1 on the right arm thereof, and operates the operation section 150 of the electronic apparatus 1 so as to input an instruction for starting right measurement to the electronic apparatus 1. The processor 120 of the electronic apparatus 1 starts to drive the atmospheric pressure sensor 112. The atmospheric pressure sensor 112 repeatedly generates atmospheric pressure data in a predetermined cycle. The processor 120 accumulates the atmospheric pressure data generated by the atmospheric pressure sensor 112 in the storage section 130 in correlation with a generation time point.

Thereafter, for example, the user swims a predetermined distance (for example, 50 m) in the crawl swimming stroke. Next, the user operates the operation section 150 of the electronic apparatus 1 so as to input an instruction for finishing the right measurement to the electronic apparatus 1. The processor 120 of the electronic apparatus 1 finishes driving of the atmospheric pressure sensor 112, and preserves atmospheric pressure data accumulated in the storage section 130 in a period from input of the starting instruction to input of the finishing instruction, in the storage section 130 as right stroke data in a predetermined format.

1-3-1-2. Left Measurement (First Example)

Next, the user mounts the electronic apparatus 1 on the left arm thereof, and operates the operation section 150 of the electronic apparatus 1 so as to input an instruction for starting left measurement to the electronic apparatus 1. The processor 120 of the electronic apparatus 1 starts to drive the atmospheric pressure sensor 112. The atmospheric pressure sensor 112 repeatedly generates atmospheric pressure data in a predetermined cycle. The processor 120 accumulates the atmospheric pressure data generated by the atmospheric pressure sensor 112 in the storage section 130 in correlation with a generation time point.

Thereafter, for example, the user swims a predetermined distance (for example, 50 m) in the crawl swimming stroke. Next, the user operates the operation section 150 of the electronic apparatus 1 so as to input an instruction for finishing the left measurement to the electronic apparatus 1.

The processor 120 of the electronic apparatus 1 finishes driving of the atmospheric pressure sensor 112, and preserves atmospheric pressure data accumulated in the storage section 130 in a period from input of the starting instruction to input of the finishing instruction, in the storage section 130 as left stroke data in a predetermined format.

1-3-1-3. Analysis (First Example)

Next, the processor 120 of the electronic apparatus 1 detects a timing at which a characteristic waveform appears in the right stroke data (time-atmospheric pressure curve). This timing is a timing at which an atmospheric pressure value takes a negative peak (valley), or an atmospheric pressure value takes a positive peak. The timing corresponds to, for example, a timing (refer to FIG. 5) called recovery of a right stroke, or a timing (refer to FIG. 5) called catch of the right stroke. The processor 120 divides the right stroke data into a plurality of partial stroke data pieces at respective detected timings, and averages waveforms of the plurality of partial stroke data pieces obtained through the division so as to compute an average trajectory of the right stroke. This trajectory indicates the tendency (habit) of the right stroke of the user (a dashed curve in FIG. 4).

Next, the processor 120 of the electronic apparatus 1 detects a timing at which a characteristic waveform appears in the left stroke data (time-atmospheric pressure curve). This timing is a timing at which an atmospheric pressure value takes a negative peak (valley), or an atmospheric pressure value takes a positive peak. The timing corresponds to, for example, a timing (refer to FIG. 5) called recovery of a left stroke, or a timing (refer to FIG. 5) called catch of the left stroke. The processor 120 divides the left stroke data into a plurality of partial stroke data pieces at respective detected timings, and averages waveforms of the plurality of partial stroke data pieces obtained through the division so as to compute an average trajectory of the left stroke. This trajectory indicates the tendency (habit) of the left stroke of the user (a solid curve in FIG. 4).

The processor 120 of the electronic apparatus 1 may perform well-known preprocessing such as noise removal on the data when analyzing the data. The processor 120 of the electronic apparatus 1 may perform a process of removing the previous and following sections for which swimming is not actually performed in the period from starting to ending of swimming on the data (this is also the same for other Examples).

1-3-1-4. Display (First Example)

The processor 120 of the electronic apparatus 1 outputs deviation between a curve as a stroke trajectory related to a temporal change in a depth of a right stroke in swimming and a curve as a stroke trajectory related to a temporal change in a depth of a left stroke, as at least one of pieces of information regarding a left-right difference. In other words, the information regarding a left-right difference displayed on the display 170 includes a graph obtained by overlapping the curve related to a temporal change in a depth of a right stroke in swimming with the curve related to a temporal change in a depth of a left stroke in swimming.

Hereinafter, details thereof will be described. The processor 120 of the electronic apparatus 1 creates an image (FIG. 4) in which a trajectory of a right stroke and a trajectory of a left stroke overlap, for example, the same graph, and displays the image on the display 170. In this case, a point corresponding to the timing in the trajectory of the right stroke and a point corresponding to the timing in the trajectory of the left stroke are positioned so as to match each other on a time axis.

Figure 4:
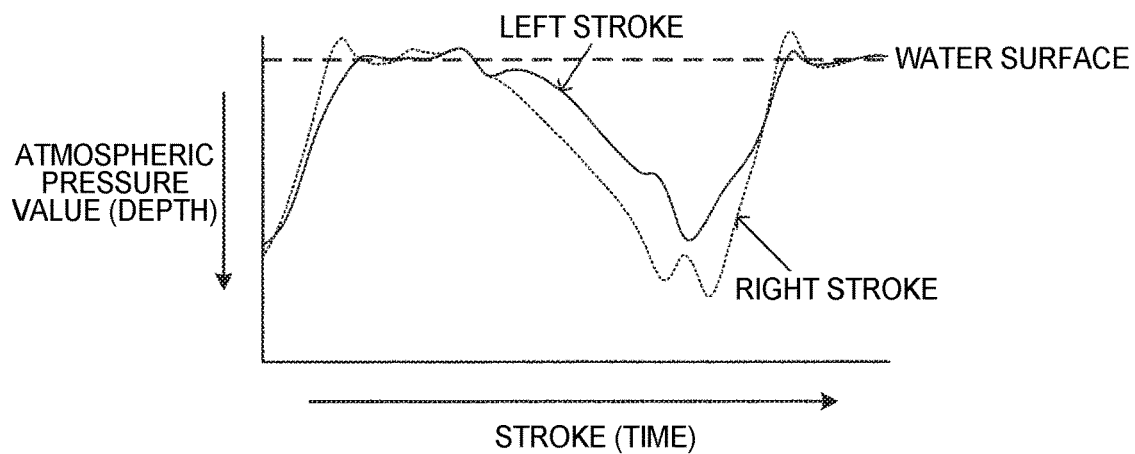
FIG. 4 illustrates an example of left-right-balance display using an atmospheric pressure sensor.
Figure 5:
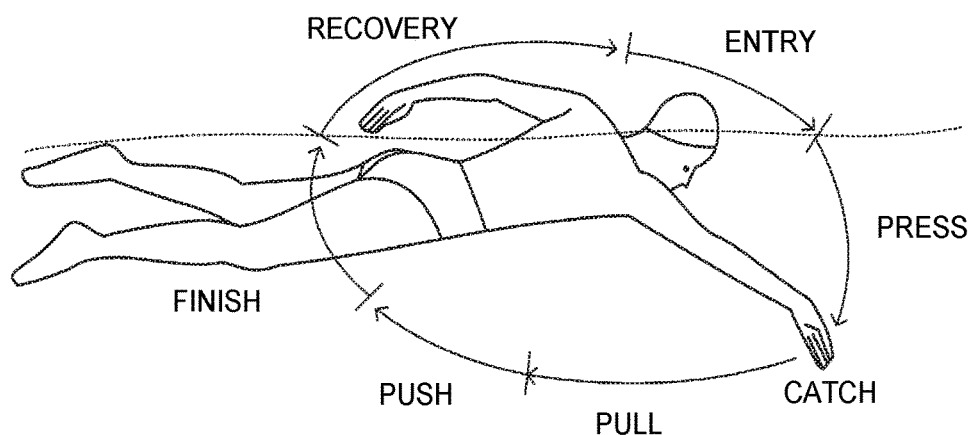
FIG. 5 illustrates an example of a diagram for explaining a stroke time.

Consequently, for example, as illustrated in FIG. 4, an image (display screen) for checking balance between left and right strokes (left-right-balance) is displayed on the display 170. The trajectory of the right stroke and the trajectory of the left stroke are displayed on the display screen in, for example, different line types so as to be easily differentiated from each other by a user. In the example illustrated in FIG. 4, the right stroke is indicated by a dotted line, and the left stroke is indicated by a solid line. Therefore, the user can check deviation between left and right stroke trajectories (left-right-balance) of the user from the display screen.

1-3-1-5. Appendix 1-3-1-5-1. Appendix of Display Content

The processor 120 of the electronic apparatus 1 displays the temporal change curve of the depth of the right stroke and the temporal change curve of the depth of the left stroke on the display 170, but may generate deviation between the two curves as a numerical value, and may display an image indicating the magnitude of the numerical value on the display 170. For example, if the numerical value is great, a text image with the content that "left-right-balance is bad" may be displayed on the display 170, and if the numerical value is small, a text image with the content that "left-right-balance is favorable" may be displayed on the display 170. Advice for improving a left-right difference may be displayed on the display 170.

1-3-1-5-2. Appendix of Display Location

In the system of the present embodiment, a display location of an image regarding left-right-balance in swimming is the display 170 of the electronic apparatus 1, but may be the display 25 of the information terminal 2. In this case, the electronic apparatus 1 may transmit display data to the information terminal 2, and the electronic apparatus 1 may transmit necessary data to the information terminal 2, and the information terminal 2 side may perform a process such as image creation. A method of transmitting data from the electronic apparatus 1 to the information terminal 2 is as described above (this is also the same for other Examples).

1-3-1-5-3. Appendix of Display Timing

In the system of the present embodiment, a process of displaying an image regarding left-right-balance in swimming is performed after measurement is finished, but may be performed during measurement (this is also the same for other Examples).

1-3-1-5-4. Upload of Measured Data

In the system of the present embodiment, the processor 120 of the electronic apparatus 1 preserves various pieces of data generated during the measurement in the storage section 130 as measured data in a predetermined format along with date-and-time data indicating the date and time of the measurement. One or a plurality of pieces of measured data stored in the storage section 130 are transmitted to the information terminal 2 so as to be stored in the storage section 24 of the information terminal 2 as necessary. The measured data stored in the storage section 24 of the information terminal 2 is uploaded to the server 4 as necessary. The measured data uploaded to the server 4 is stored in the storage section 44 of the server 4. The measured data at various dates and times of various users stored in the storage section 44 of the server 4 are managed for each user for each date and time by the processor 41 of the server 4. Communication between the electronic apparatus 1 and the information terminal 2 is performed via the communicator 190 of the electronic apparatus 1 and the communicator 22 of the information terminal 2, and communication between the information terminal 2 and the server 4 is performed via the communicator 27 of the information terminal 2, the network 3, and the communicator 42 of the server 4 (this is also the same for other Examples).

1-3-2. Left-Right-Balance Display Process Using Head Acceleration Sensor (Second Example)

The processor 120 of the electronic apparatus 1 may output a difference between the time required for a right stroke in swimming and the time required for a left stroke, as at least one of pieces of information regarding a left-right difference. The information regarding a left-right difference displayed on the display 170 of the electronic apparatus 1 may include a graph indicating the difference between the time required for a right stroke in swimming and the time required for a left stroke in swimming.

Hereinafter, details thereof will be described. Herein, a description will be made of an example in which the sensor device 1C is used for measurement, and the electronic apparatus 1 is used for analysis and display. In this case, the electronic apparatus 1 and the sensor device 1C perform direct communication with each other via the communicator 190 and the communicator 190C.

1-3-2-1. Measurement (Second Example)

Figure 6:
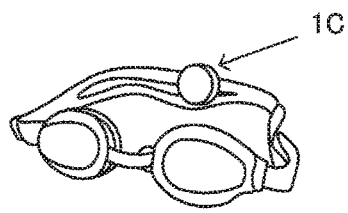
FIG. 6 illustrates an example of a diagram for explaining a method of mounting the sensor device on the head of a user.

The user mounts the sensor device 1C on the head thereof. If the user uses a goggle, for example, as illustrated in FIG. 6, the sensor device 1C may be attached to the center (the so-called back of the head) of a belt strap made of rubber. The user operates the operation section 150 of the electronic apparatus 1 so as to input an instruction for starting measurement to the electronic apparatus 1. The processor 120 of the electronic apparatus 1 transmits the measurement starting instruction to the sensor device 1C via the communicator 190.

If the processor 120C of the sensor device 1C receives the measurement starting instruction via the communicator 190C, driving of the acceleration sensor 113C is started. The acceleration sensor 113C repeatedly generates acceleration data in a predetermined cycle. The processor 120C accumulates the acceleration data generated by the acceleration sensor 113C in the storage section 130C in correlation with a generation time point.

Thereafter, for example, the user swims a predetermined distance (for example, 50 m) in the crawl swimming stroke. Next, the user operates the operation section 150 of the electronic apparatus 1 so as to input an instruction for finishing the measurement to the electronic apparatus 1. The processor 120 of the electronic apparatus 1 transmits the measurement finishing instruction to the sensor device 1C via the communicator 190.

If the measurement finishing instruction is received via the communicator 190C, the processor 120C of the sensor device 1C finishes the driving of the acceleration sensor 113C, and preserves acceleration data accumulated in the storage section 130C in a period from input of the starting instruction to input of the finishing instruction, in the storage section 130C as stroke data in a predetermined format. The processor 120C of the sensor device 1C transmits the stroke data to the electronic apparatus 1 via the communicator 190C. The processor 120 of the electronic apparatus 1 receives the stroke data (FIGS. 10, 11 and 12) via the communicator 190.

1-3-2-2. Analysis (Second Example)

Figure 10:
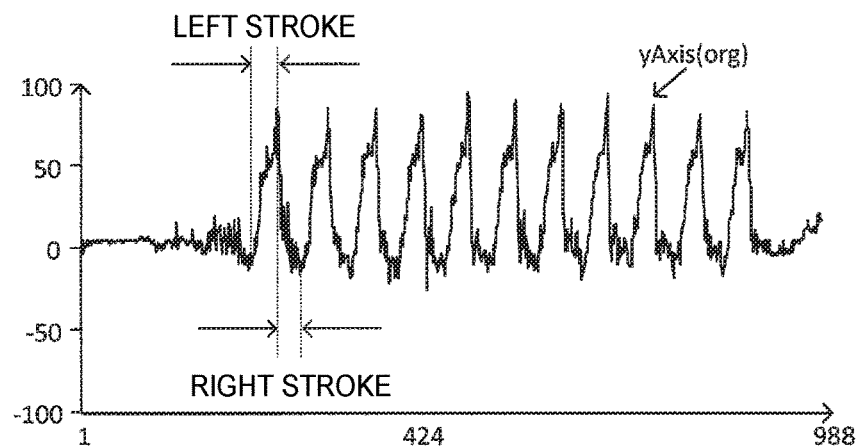
FIG. 10 illustrates an example of a graph illustrating a y axis component (a component in a direction directed from the right shoulder of the user toward the left shoulder thereof) of three-axis acceleration data from the sensor device mounted on the head.
Figure 11:
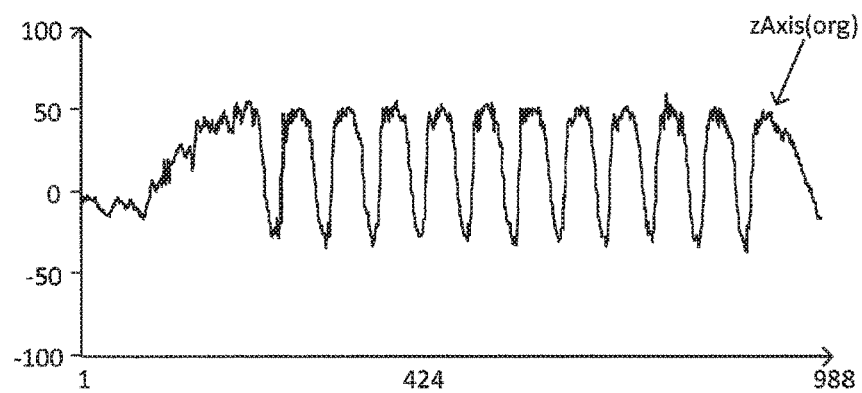
FIG. 11 illustrates an example of a graph illustrating a z axis component (a component in a direction directed from the chest of the user toward the back thereof) of the three-axis acceleration data from the sensor device mounted on the head.
Figure 12:
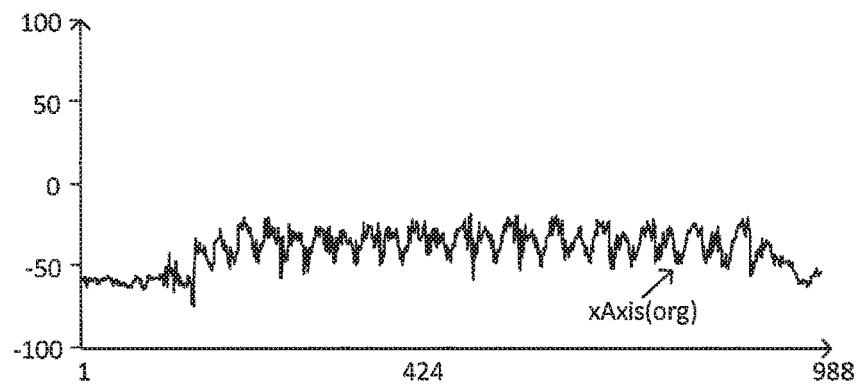
FIG. 12 illustrates an example of a graph illustrating an x axis component (a component in a direction directed from the top of the head of the user toward the throat thereof) of the three-axis acceleration data from the sensor device mounted on the head.

Next, the processor 120 of the electronic apparatus 1 extracts a y axis component (a component in a direction directed from the right shoulder of the user toward the left shoulder thereof, and a component illustrated in FIG. 10) from the stroke data (FIGS. 10, 11 and 12). In a case where the sensor device 1C is mounted on the head of the user in a predefined attitude, the processor 120 may extract a component in a predetermined direction included in the stroke data as the y axis component. In a case where an attitude of the sensor device 1C is unknown, the processor 120 may extract a component in a direction in which a characteristic waveform (refer to FIG. 10) appears in the stroke data, as the y axis component.

Next, the processor 120 of the electronic apparatus 1 detects, as a left stroke period, a period from a timing at which an acceleration value takes a negative peak (valley) to the next timing at which an acceleration value takes a positive peak (a period with "left stroke" in FIG. 10), and detects, as a right stroke period, a period from a timing at which an acceleration value takes a positive peak to the next timing at which an acceleration value takes a negative peak (valley) (a period with "right stroke" in FIG. 10), in the extracted y axis component.

Next, the processor 120 of the electronic apparatus 1 calculates an average value (average right stroke time) of lengths of the right stroke periods, and calculates an average value (average left stroke time) of lengths of the left stroke periods.

The processor 120 of the electronic apparatus 1 may detect, for example, a timing at which an acceleration value takes a positive peak and a timing at which an acceleration value takes a negative peak (valley) in an x axis component (FIG. 11) of the stroke data (three-axis acceleration data) so as to detect a timing at which a peak considerably increases (for example, the magnitude of the peak exceeds a threshold value) as a rest timing, and may count the number of times of breathing taken from measurement starting to measurement ending.

Extraction of the x axis component (a component in a direction directed from the top of the head to the throat of the user) is performed, for example, as follows. In other words, in a case where the sensor device 1C is mounted on the head of the user in a predefined attitude, the processor 120 of the electronic apparatus 1 may extract a component in a predetermined direction included in the stroke data as the x axis component. In a case where an attitude of the sensor device 1C is unknown, the processor 120 may extract a component in a direction in which a characteristic waveform (refer to FIG. 11) appears in the stroke data, as the x axis component.

Here, the x axis component is used to detect a rest timing, but the y axis component may be used instead of the x axis component.

The processor 120 of the electronic apparatus 1 calculates a ratio $R_R$ of the time required for the right stroke according to, for example, an equation of $R_R [\%]=100 \times T_R/(T_R+T_L)$ [%] on the basis of the average right stroke time $T_R$ and the average left stroke time $T_L$.

Similarly, the processor 120 of the electronic apparatus 1 calculates a ratio $R_L$ of the time required for the left stroke according to, for example, an equation of $R_L [\%]=100 \times T_L/(T_R+T_L)$ [%] on the basis of the average right stroke time $T_R$ and the average left stroke time $T_L$.

The processor 120 of the electronic apparatus 1 may perform well-known preprocessing such as noise removal on the data when analyzing the data. The processor 120 of the electronic apparatus 1 may perform a process of removing the previous and following sections for which swimming is not actually performed in the period from starting to ending of swimming on the data.

1-3-2-3. Display (Second Example)

Figure 17:
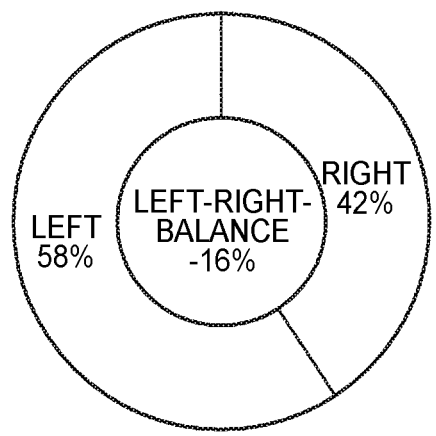
FIG. 17 illustrates an example of left-right-balance display.

The processor 120 of the electronic apparatus 1 creates an image (FIG. 17) in which balance (left-right-balance) between the ratios $R_R$ and $R_L$ is indicated by, for example, a pie chart, and displays the image on the display 170. In the example illustrated in FIG. 17, a numerical value of the left-right-balance $\Delta=R_R-R_L$ is displayed at the center of the pie chart.

Herein, a mounting location of the sensor device 1C is the head of the user, but information regarding a left-right difference can be similarly acquired even in a case of the waist of the user. A method of mounting the sensor device 1C on the waist of the user will be described later.

Herein, the head acceleration sensor is used to measure left-right-balance, but left-right-balance may be measured by using an arm atmospheric pressure sensor.

1-3-3. Left-Right-Balance Display Process Using Waist Acceleration Sensor (Third Example)

The processor 120 of the electronic apparatus 1 may output a difference between driving force based on a right stroke in swimming and driving force based on a left stroke in the swimming as at least one of the pieces of information regarding a left-right difference. The information regarding a left-right difference displayed on the display 170 may include a graph indicating the difference between the driving force based on a right stroke in swimming and the driving force based on a left stroke in swimming.

The processor 120 of the electronic apparatus 1 may calculate deviation relative to a predetermined straight advancing direction due to a difference between driving force based on a right stroke in swimming and driving force based on a left stroke in the swimming, and may output the extent of the calculated deviation as at least one of the pieces of information regarding a left-right difference. The information regarding a left-right difference displayed on the display 170 may include a graph indicating deviation relative to a predetermined straight advancing direction due to the difference between the driving force based on a right stroke in swimming and the driving force based on a left stroke in swimming.

Hereinafter, details thereof will be described. Herein, a description will be made of an example in which the sensor device 1C is used for measurement, and the electronic apparatus 1 is used for analysis and display. In this case, the electronic apparatus 1 and the sensor device 1C perform communication with each other via the communicator 190 and the communicator 190C.

1-3-3-1. Measurement (Third Example)

Figure 7:
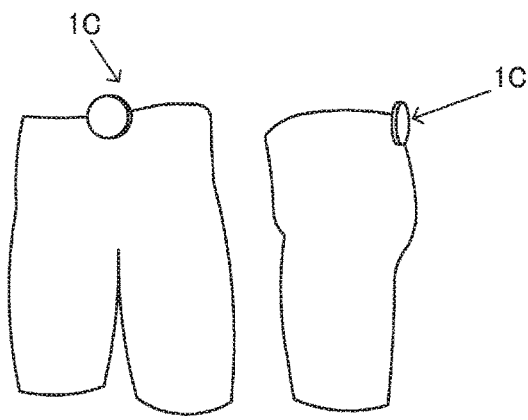
FIG. 7 illustrates an example of a diagram for explaining a method of mounting the sensor device on the waist of the user.

The user mounts the sensor device 1C on the waist thereof. For example, as illustrated in FIG. 7, a mounting location of the sensor device 1C is the center of the belly surface side or the back surface side of the waist. The user operates the operation section 150 of the electronic apparatus 1 so as to input an instruction for starting measurement to the electronic apparatus 1. The processor 120 of the electronic apparatus 1 transmits the measurement starting instruction to the sensor device 1C via the communicator 190.

If the processor 120C of the sensor device 1C receives the measurement starting instruction via the communicator 190C, driving of the acceleration sensor 113C is started. The acceleration sensor 113C repeatedly generates acceleration data in a predetermined cycle. The processor 120C accumulates the acceleration data generated by the acceleration sensor 113C in the storage section 130C in correlation with a generation time point.

Thereafter, for example, the user swims a predetermined distance (for example, 50 m) in the crawl swimming stroke. Next, the user operates the operation section 150 of the electronic apparatus 1 so as to input an instruction for finishing the measurement to the electronic apparatus 1. The processor 120 of the electronic apparatus 1 transmits the measurement finishing instruction to the sensor device 1C via the communicator 190.

If the measurement finishing instruction is received via the communicator 190C, the processor 120C of the sensor device 1C finishes the driving of the acceleration sensor 113C, and preserves acceleration data accumulated in the storage section 130C in a period from input of the starting instruction to input of the finishing instruction, in the storage section 130C as stroke data in a predetermined format. The processor 120C of the sensor device 1C transmits the stroke data to the electronic apparatus 1 via the communicator 190C. The processor 120 of the electronic apparatus 1 receives the stroke data (FIGS. 13, 14 and 15) via the communicator 190.

1-3-3-2. Analysis (Third Example)

Figure 13:
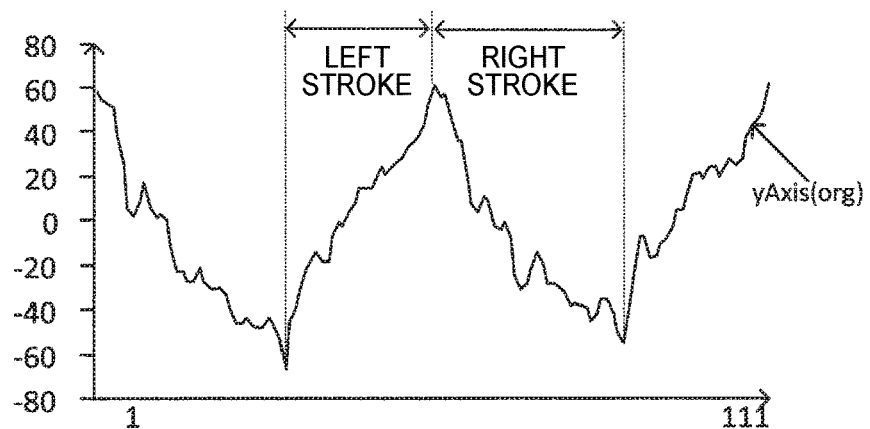
FIG. 13 illustrates an example of a graph illustrating a y axis component (a component in a direction directed from the right flank of the user toward the left flank thereof) of three-axis acceleration data from the sensor device mounted on the waist.
Figure 14:
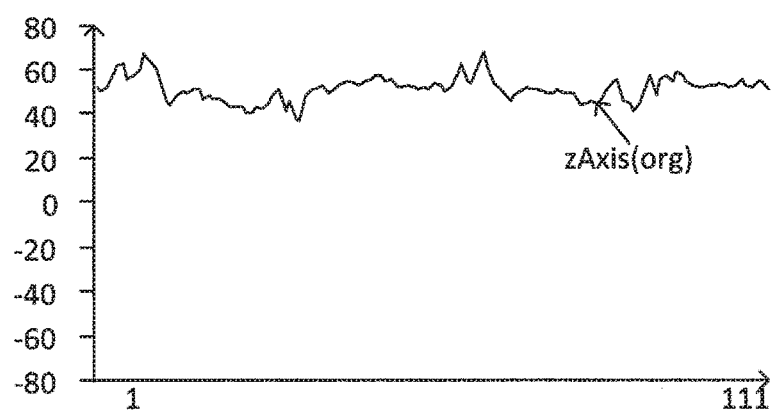
FIG. 14 illustrates an example of a graph illustrating a z axis component (a component in a direction directed from the chest of the user toward the back thereof) of the three-axis acceleration data from the sensor device mounted on the waist.
Figure 15:
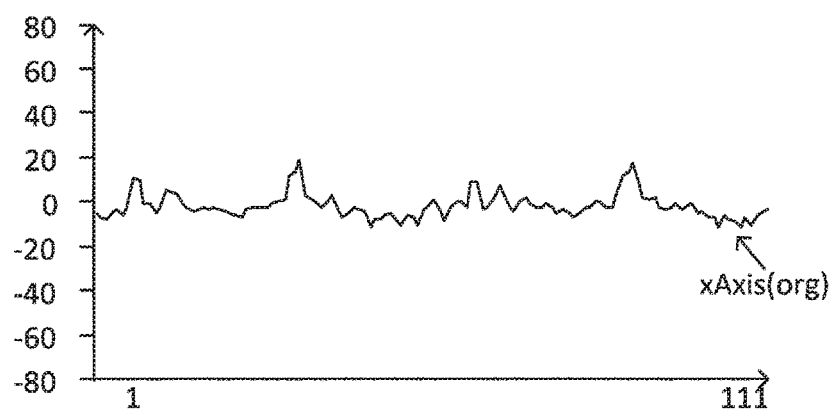
FIG. 15 illustrates an example of a graph illustrating an x axis component (a component in a direction directed from the neck toward the waist along the spine of the user) of the three-axis acceleration data from the sensor device mounted on the waist.

Next, the processor 120 of the electronic apparatus 1 extracts a y axis component (a component in a direction directed from the right flank of the user toward the left flank thereof, and a component illustrated in FIG. 13) from the stroke data (FIGS. 13, 14 and 15). In a case where the sensor device 1C is mounted on the waist of the user in a predefined attitude, the processor 120 may extract a component in a predetermined direction included in the stroke data as the y axis component. In a case where an attitude of the sensor device 1C is unknown, the processor 120 may extract a component in a direction in which a characteristic waveform (refer to FIG. 13) appears in the stroke data, as the y axis component.

The processor 120 of the electronic apparatus 1 extracts an x axis component (a component in a direction directed from the neck toward the waist along the spine of the user) from the stroke data (FIGS. 13, 14 and 15). In a case where the sensor device 1C is mounted on the waist of the user in a predefined attitude, the processor 120 may extract a component in a predetermined direction included in the stroke data as the x axis component. In a case where an attitude of the sensor device 1C is unknown, the processor 120 may extract a component in a direction in which a characteristic waveform (refer to FIG. 15) appears in the stroke data, as the x axis component.

Next, the processor 120 of the electronic apparatus 1 detects, as a left stroke period, a period from a timing at which an acceleration value takes a negative peak (valley) to the next timing at which an acceleration value takes a positive peak (a period with "left stroke" in FIG. 13), and detects, as a right stroke period, a period from a timing at which an acceleration value takes a positive peak to the next timing at which an acceleration value takes a negative peak (valley) (a period with "right stroke" in FIG. 13), in the extracted y axis component.

Figure 16:
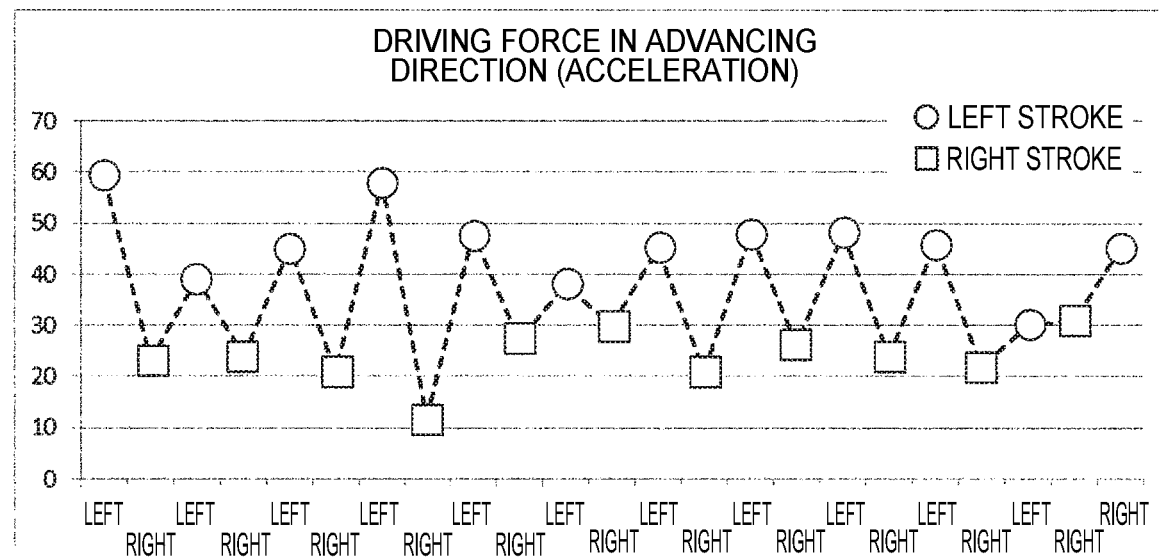
FIG. 16 illustrates an example of a graph for comparing driving force in an advancing direction in a right stroke with driving force in the advancing direction in a left stroke.

The processor 120 of the electronic apparatus 1 calculates a value corresponding to the magnitude of the x axis component in the right stroke period as driving force $\alpha_R$ based on a right stroke, and calculates value corresponding to the magnitude of the x axis component in the left stroke period as driving force $\alpha_L$ based on a left stroke. FIG. 16 is a diagram in which the driving force $\alpha_R$ based on each right stroke and the driving force $\alpha_L$ based on each left stroke are visualized. In FIG. 16, a value of the driving force $\alpha_R$ based on each right stroke is plotted with a square mark, and a value of the driving force $\alpha_L$ based on each left stroke is plotted with a circular mark.

The processor 120 of the electronic apparatus 1 calculates an average value (average right stroke driving force) $A_R$ of the driving force $\alpha_R$ based on each right stroke, and an average value (average left stroke driving force) $A_L$ of the driving force $\alpha_L$ based on each left stroke.

The processor 120 of the electronic apparatus 1 calculates a ratio $R_R$ of driving force based on the right stroke according to, for example, an equation of $R_R$ [%]=100×$A_R$/($A_R$+$A_L$) [%] on the basis of the average right stroke driving force $A_R$ and the average left stroke driving force $A_L$.

Similarly, the processor 120 of the electronic apparatus 1 calculates a ratio $R_L$ of driving force based on the left stroke according to an equation of $R_L$ [%]=100×$A_L$/($A_R$+$A_L$) [%] on the basis of the average right stroke driving force $A_R$ and the average left stroke driving force $A_L$.

Figure 8:
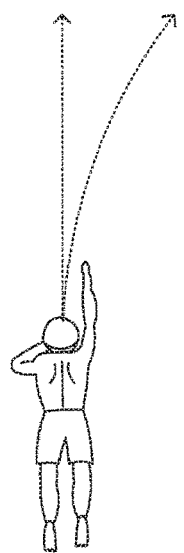
FIG. 8 illustrates an example of a diagram for explaining an advancing direction of the user during swimming.
Figures 9A, 9B:
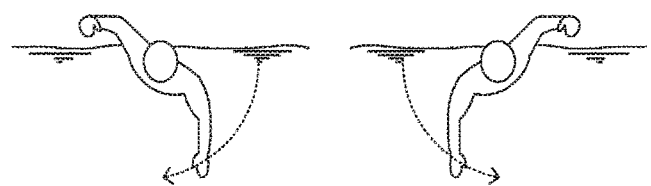
FIGS. 9A and 9B illustrate examples of diagrams for explaining rolling of the user during swimming.
Figure 18:
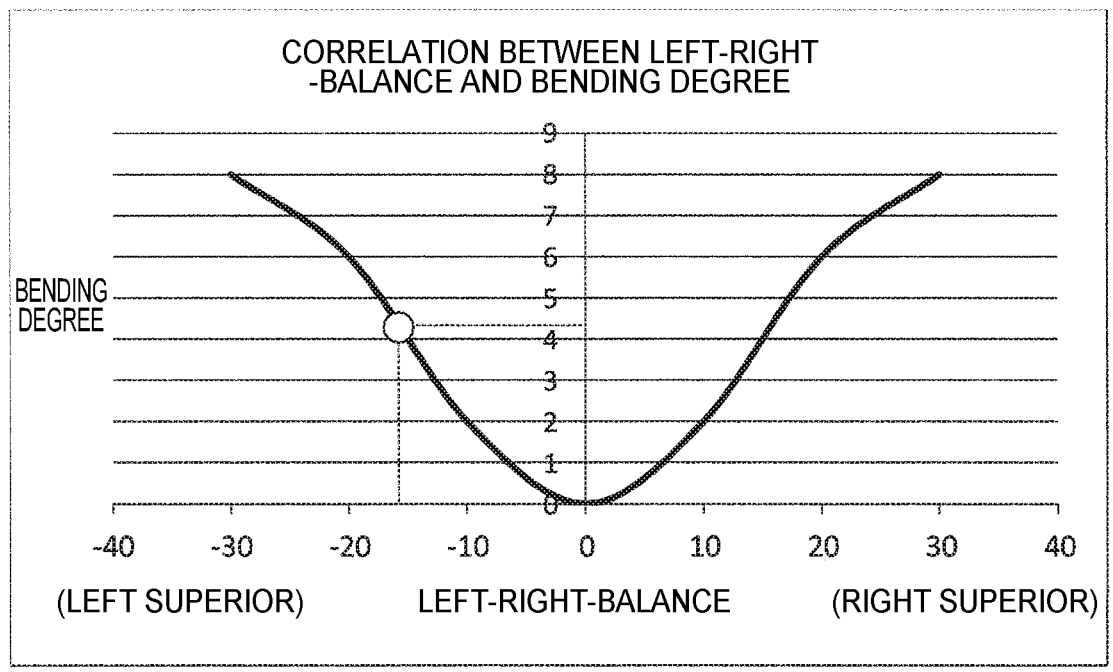
FIG. 18 illustrates an example of a graph illustrating a correlation between left-right-balance and a bent angle.

The processor 120 of the electronic apparatus 1 calculates balance (left-right-balance) Δ between the ratios $R_R$ and $R_L$ according to, for example, an equation of Δ=$R_R$−$R_L$, and calculates a bending degree of the user by applying the left-right-balance Δ to a predetermined correlation characteristic (refer to FIG. 18). The bending degree is information indicating the extent of deviation (FIG. 8) relative to a straight advancing direction (x axis direction). The correlation characteristic (FIG. 18), which indicates a relationship between the left-right-balance Δ and the bending degree, is formed of a function, a lookup table, or the like, and is stored in, for example, the storage section 130 of the electronic apparatus 1. The correlation characteristic (FIG. 18) is prepared in advance on the basis of actually measured data of the left-right-balance Δ of various users and actually measured data of the extent of deviation relative to a straight advancing direction.

The processor 120 of the electronic apparatus 1 may perform well-known preprocessing such as noise removal on the data when analyzing the data. The processor 120 of the electronic apparatus 1 may perform a process of removing the previous and following sections for which swimming is not actually performed in the period from starting to ending of swimming on the data.

1-3-3-3. Display (Third Example)

The processor 120 of the electronic apparatus 1 creates an image (FIG. 17) in which balance (left-right-balance) between the ratios $R_R$ and $R_L$ is indicated by, for example, a pie chart, and displays the image on the display 170. In the example illustrated in FIG. 17, a numerical value of the left-right-balance Δ=$R_R$−$R_L$ is displayed at the center of the pie chart.

The processor 120 of the electronic apparatus 1 displays a text image indicating a value of the bending degree obtained on the basis of the left-right-balance Δ, on the display 170. The bending degree may be indicated by a curve image (refer to FIG. 8) instead of being indicated by a numerical value.

1-3-4. Other Left-Right-Balance Display Processes 1-3-4-1. Left-Right-Balance Display Process Based on Rolling (Fourth Example)

The processor 120 of the electronic apparatus 1 may output a difference between time for which the body is rolling to the right arm side and time for which the body is rolling to the left arm side, with an advancing direction in swimming as a rotation axis, as at least one of the pieces of information regarding a left-right difference. The information regarding a left-right difference displayed on the display 170 may include a graph indicating the difference between time for which the body is rolling to the right arm side and time for which the body is rolling to the left arm side, with an advancing direction in swimming as a rotation axis.

Hereinafter, details thereof will be described. Herein, a description will be made of an example in which the sensor device 1C is used for measurement, and the electronic apparatus 1 is used for analysis and display. In this case, the electronic apparatus 1 and the sensor device 1C perform communication with each other via the communicator 190 and the communicator 190C. Herein, a difference with a left-right-balance display process using the waist acceleration sensor will be focused, and other descriptions will be omitted.

Rolling mentioned here is rotation about the x axis of the user's body, and the processor 120 of the electronic apparatus 1 may detect whether or not rolling about the x axis is performed and a direction of rolling (a positive direction or a negative direction) on the basis of, for example, acceleration data (stroke data) generated by the acceleration sensor 113C (or the acceleration sensor 113). A differentiation between the positive direction and the negative direction indicates a differentiation of whether the user's body is rolling to the right (right arm side) or is rolling to the left (left arm side).

The processor 120 of the electronic apparatus 1 calculates a length $T_R'$ of a period in which the user's body is rolling to the right and a length $T_L'$ of a period in which the user's body is rolling to the left on the basis of stroke data, and calculates a ratio $R_R$ of a right rolling period according to, for example, an equation of $R_R$ [%]=100×$T_R'$/($T_R'$+$T_L'$).

Similarly, the processor 120 of the electronic apparatus 1 calculates a ratio $R_L$ of a left rolling period according to, for example, an equation of $R_L$ [%]=100×$T_L'$/($T_R'$+$T_L'$) on the basis of the length $T_R'$ of a period in which the user's body is rolling to the right and the length $T_L'$ of a period in which the user's body is rolling to the left by using the stroke data.

The processor 120 of the electronic apparatus 1 creates an image (FIG. 17) in which balance (left-right-balance) between the ratios $R_R$ and $R_L$ is indicated by, for example, a pie chart, and displays the image on the display 170. In the example illustrated in FIG. 17, a numerical value of the left-right-balance Δ=$R_R$−$R_L$ is displayed at the center of the pie chart.

1-3-4-2. Left-Right-Balance Display Process Regarding Flutter Kick (Fifth Example)

In the embodiment, the crawl is assumed as a swimming stroke of the user in the left-right-balance display process using the waist acceleration sensor, but flutter kick may be performed in a state in which both hands are not moved. In this case, the user may check a difference between driving force based on a left kick and driving force based on a right kick in the flutter kick. Information (swimming stroke type) regarding a swimming stroke employed by the user may be manually input to the electronic apparatus 1 by the user, and may be detected by the processor 120 of the electronic apparatus 1 on the basis of a sensor output.

1-4. Description of Flow 1-4-1. Flow of Left-Right-Balance Display Process Using Arm Atmospheric Pressure Sensor (First Example)

Figure 19:
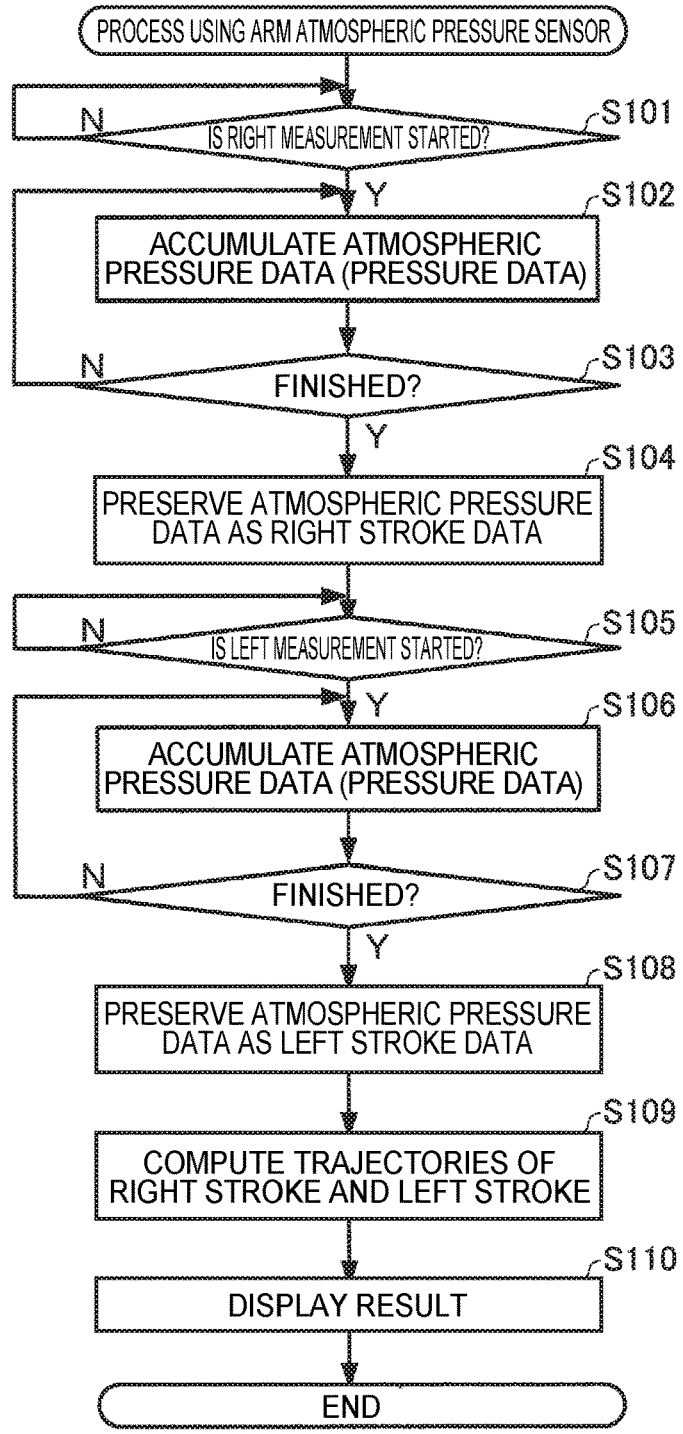
FIG. 19 illustrates an example of a flowchart of a left-right-balance display process using an arm atmospheric pressure sensor.

FIG. 19 illustrates an example of a flowchart illustrating a left-right-balance display process using an arm atmospheric pressure sensor. Hereinafter, each step in FIG. 19 will be described in order. The order of execution of the steps in FIG. 19 may be replaced with each other in an allowable range.

First, the processor 120 of the electronic apparatus 1 determines whether or not a right measurement starting instruction is input from the user (S101), repeatedly performs the determination (S101) in a case where the instruction is not input (S101N), and proceeds to the next process in a case where the instruction is input (S101Y).

Next, the processor 120 of the electronic apparatus 1 drives the atmospheric pressure sensor 112 (S102). Atmospheric pressure data generated by the atmospheric pressure sensor 112 is accumulated in the storage section 130.

Next, the processor 120 of the electronic apparatus 1 determines whether or not a finishing instruction is input from the user (S103), performs step S102 again in a case where the instruction is not input (S103N), and proceeds to the next process in a case where the instruction is input (S103Y).

Next, the processor 120 of the electronic apparatus 1 preserves the atmospheric pressure data accumulated in the storage section 130, in the storage section 130 as right stroke data in a predetermined format (S104).

Next, the processor 120 of the electronic apparatus 1 determines whether or not a left measurement starting instruction is input from the user (S105), repeatedly performs the determination (S105) in a case where the instruction is not input (S105N), and proceeds to the next process in a case where the instruction is input (S105Y).

Next, the processor 120 of the electronic apparatus 1 drives the atmospheric pressure sensor 112 (S106). Atmospheric pressure data generated by the atmospheric pressure sensor 112 is accumulated in the storage section 130.

Next, the processor 120 of the electronic apparatus 1 determines whether or not a finishing instruction is input from the user (S107), performs step S106 again in a case where the instruction is not input (S107N), and proceeds to the next process in a case where the instruction is input (S107Y).

Next, the processor 120 of the electronic apparatus 1 preserves the atmospheric pressure data accumulated in the storage section 130, in the storage section 130 as left stroke data in a predetermined format (S108).

Next, the processor 120 of the electronic apparatus 1 computes an average trajectory of right strokes and an average trajectory of left strokes on the basis of the right stroke data (time-atmospheric pressure curve) and the left stroke data (time-atmospheric pressure curve) (S109).

Next, the processor 120 of the electronic apparatus 1 creates an image (FIG. 4) in which the average trajectory of the right strokes overlaps the average trajectory of the left strokes, for example, on the same graph, displays the image on the display 170 (S110), and finishes the flow.

1-4-2. Flow of Left-Right-Balance Display Process Using Head Acceleration Sensor (Second Example)

Figure 20:
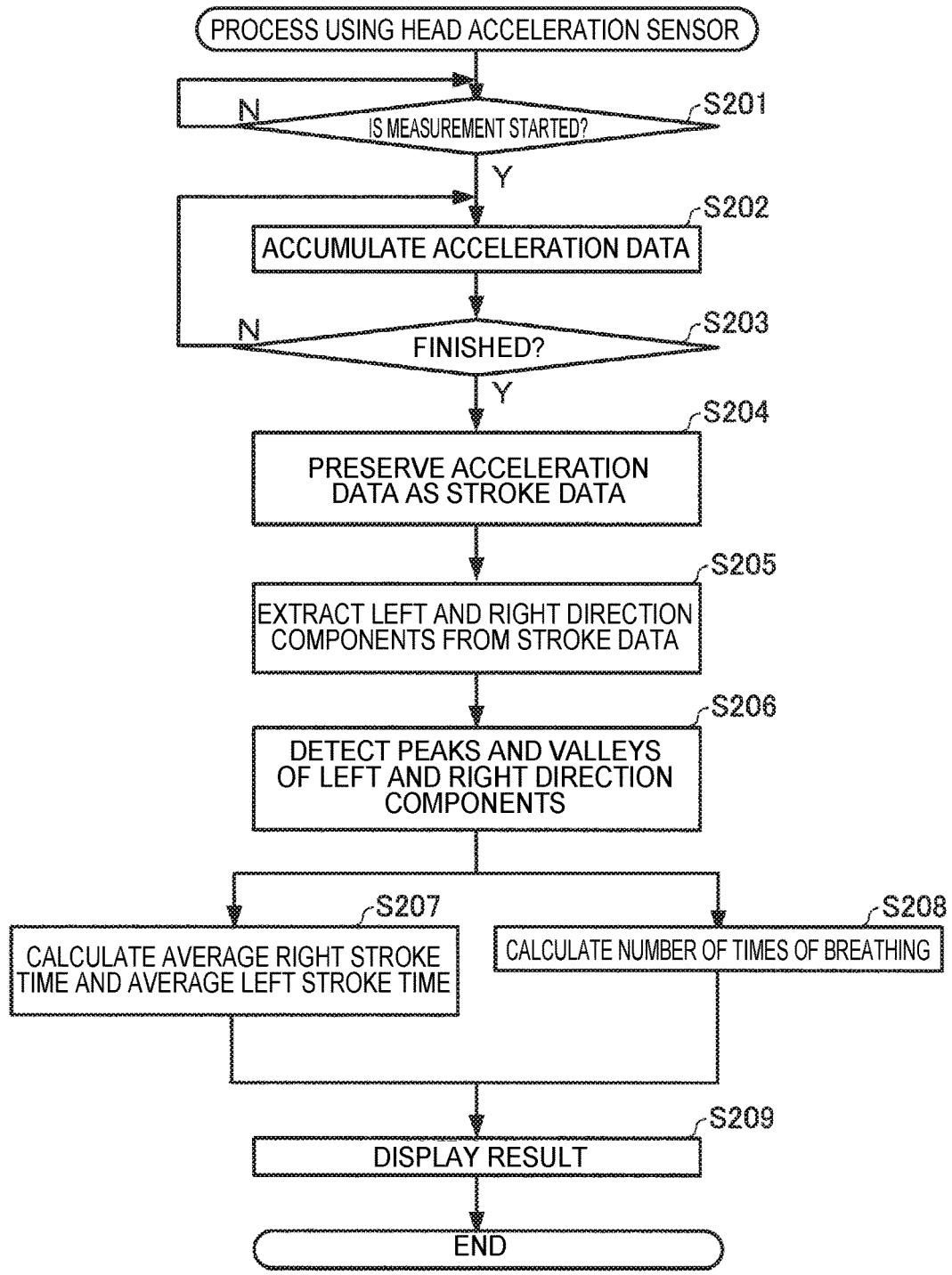
FIG. 20 illustrates an example of a flowchart of a left-right-balance display process using a head acceleration sensor.

FIG. 20 illustrates an example of a flowchart illustrating a left-right-balance display process using a head acceleration sensor. Hereinafter, each step in FIG. 20 will be described in order. The order of execution of the steps in FIG. 20 may be replaced with each other in an allowable range.

First, the processor 120 of the electronic apparatus 1 determines whether or not a measurement starting instruction is input from the user (S201), repeatedly performs the determination (S201) in a case where the instruction is not input (S201N), and proceeds to the next process in a case where the instruction is input (S201Y).

Next, the processor 120 of the electronic apparatus 1 transmits the measurement starting instruction to the sensor device 1C, so as to drive the acceleration sensor 113C of the sensor device 1C (S202). Acceleration data generated by the acceleration sensor 113C is accumulated in the storage section 130C.

Next, the processor 120 of the electronic apparatus 1 determines whether or not a finishing instruction is input from the user (S203), performs step S202 again in a case where the instruction is not input (S203N), and proceeds to the next process in a case where the instruction is input (S203Y).

Next, the processor 120 of the electronic apparatus 1 transmits the measurement finishing instruction to the sensor device 1C (S204). The processor 120C of the sensor device 1C preserves the acceleration data accumulated in the storage section 130C, in the storage section 130C as stroke data in a predetermined format, and transmits the stroke data to the electronic apparatus 1.

Next, the processor 120 of the electronic apparatus 1 extracts a y axis component (a component in a direction directed from the right shoulder of the user toward the left shoulder thereof, and a component illustrated in FIG. 10) from the stroke data (time-acceleration curve) received from the sensor device 1C (S205).

Next, the processor 120 of the electronic apparatus 1 detects a peak and a valley of the extracted y axis component (S206).

Next, the processor 120 of the electronic apparatus 1 calculates average right stroke time $T_R$ and average left stroke time $T_L$ on the basis of the detected peak and valley (S207).

The processor 120 of the electronic apparatus 1 calculates the number of times of breathing on the basis of the stroke data received from the electronic apparatus 1 (S208).

Next, the processor 120 of the electronic apparatus 1 creates an image (FIG. 17) such as a pie chart indicating the left-right-balance $\Delta$ of the average right stroke time $T_R$ and the average left stroke time $T_L$, displays the image on the display 170 (S209), and finishes the flow. The image may include the number of times of breathing calculated in step S208. The number of times of breathing may be indicated by, for example, a text image indicating a numerical value.

1-4-3. Flow of Left-Right-Balance Display Process Using Waist Acceleration Sensor (Third Example)

Figure 21:
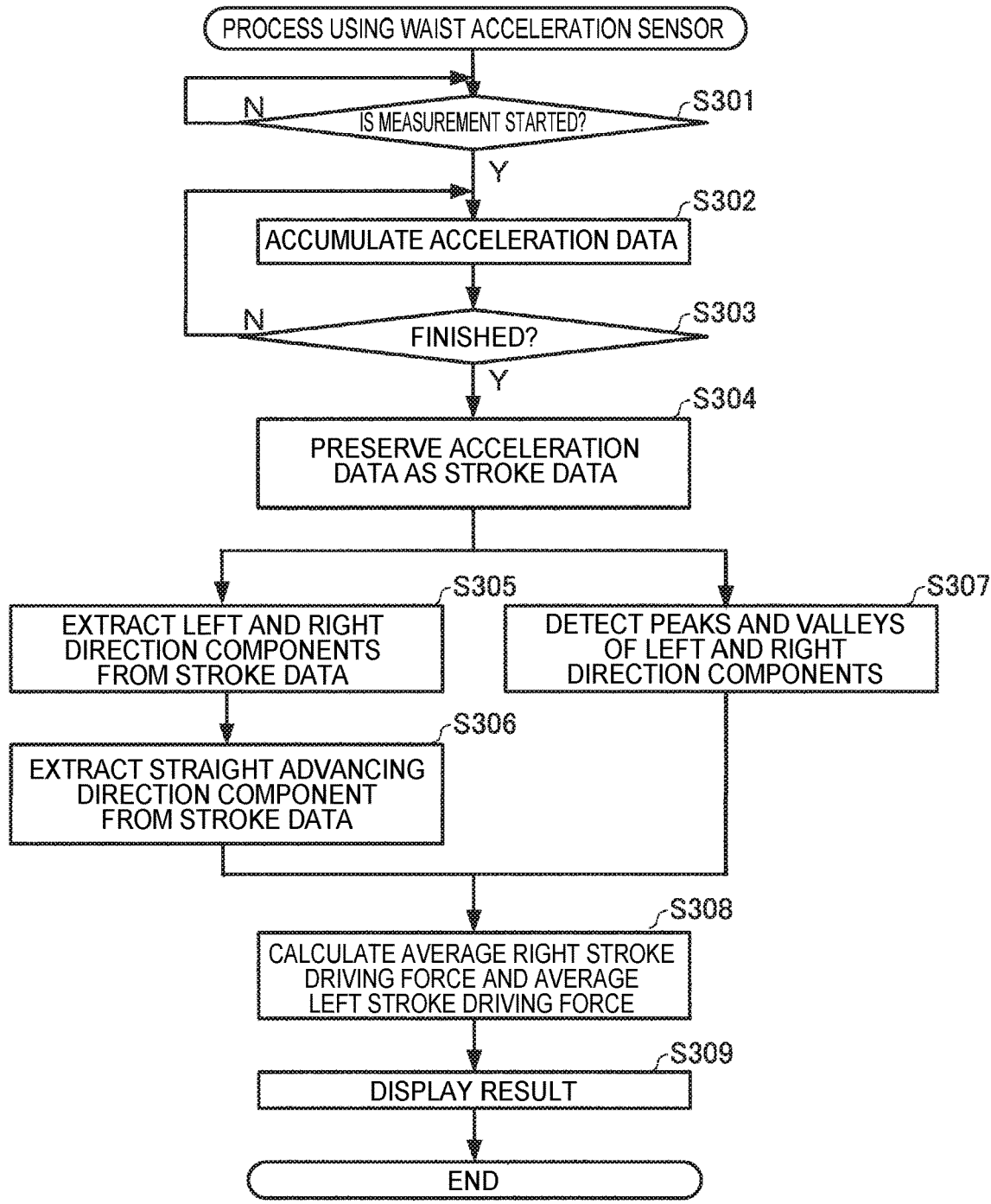
FIG. 21 illustrates an example of a flowchart of a left-right-balance display process using a waist acceleration sensor.

FIG. 21 illustrates an example of a flowchart illustrating a left-right-balance display process using a waist acceleration sensor. Hereinafter, each step in FIG. 21 will be described in order. The order of execution of the steps in FIG. 21 may be replaced with each other in an allowable range.

First, the processor 120 of the electronic apparatus 1 determines whether or not a measurement starting instruction is input from the user (S301), repeatedly performs the determination (S301) in a case where the instruction is not input (S301N), and proceeds to the next process in a case where the instruction is input (S301Y).

Next, the processor 120 of the electronic apparatus 1 transmits the measurement starting instruction to the sensor device 1C, so as to drive the acceleration sensor 113C of the sensor device 1C (S302). Acceleration data generated by the acceleration sensor 113C is accumulated in the storage section 130C.

Next, the processor 120 of the electronic apparatus 1 determines whether or not a finishing instruction is input from the user (S303), performs step S302 again in a case where the instruction is not input (S303N), and proceeds to the next process in a case where the instruction is input (S303Y).

Next, the processor 120 of the electronic apparatus 1 transmits the measurement finishing instruction to the sensor device 1C (S304). The processor 120C of the sensor device 1C preserves the acceleration data accumulated in the storage section 130C, in the storage section 130C as stroke data in a predetermined format, and transmits the stroke data to the electronic apparatus 1.

Next, the processor 120 of the electronic apparatus 1 extracts a y axis component (a component in a direction directed from the right flank of the user toward the left flank thereof, and a component illustrated in FIG. 10) from the stroke data (time-acceleration curve) (S305).

Next, the processor 120 of the electronic apparatus 1 detects a peak and a valley of the extracted y axis component (S306).

The processor 120 of the electronic apparatus 1 extracts an x axis component (a component in a direction directed from the neck toward the waist along the spine of the user) from the stroke data (time-acceleration curve) (S307).

Next, the processor 120 of the electronic apparatus 1 calculates an average value (average right stroke driving force) $A_R$ of the driving force $\alpha_R$ based on a right stroke and an average value (average left stroke driving force) $A_L$ of the driving force $\alpha_L$ based on a left stroke on the basis of a timing of the peak, a timing of the valley, and the magnitude of the x axis component (S308).

Next, the processor 120 of the electronic apparatus 1 creates an image (FIG. 17) such as a pie chart indicating balance (left-right-balance) $\Delta$ of $A_R$ and $A_L$, displays the image on the display 170 (S308), and finishes the flow. The image may include information regarding a bending degree which is estimated on the basis of the left-right-balance. The information regarding a bending degree may be indicated by, for example, a text image indicating a numerical value.

1-5. Description of Advice Function 1-5-1. Advice on Number of Times of Breathing (Second Example)

The processor 120 of the electronic apparatus 1 may give the user, for example, advice on the basis of the number of times of breathing measured in the left-right-balance display process using the head acceleration sensor.

Figure 22:
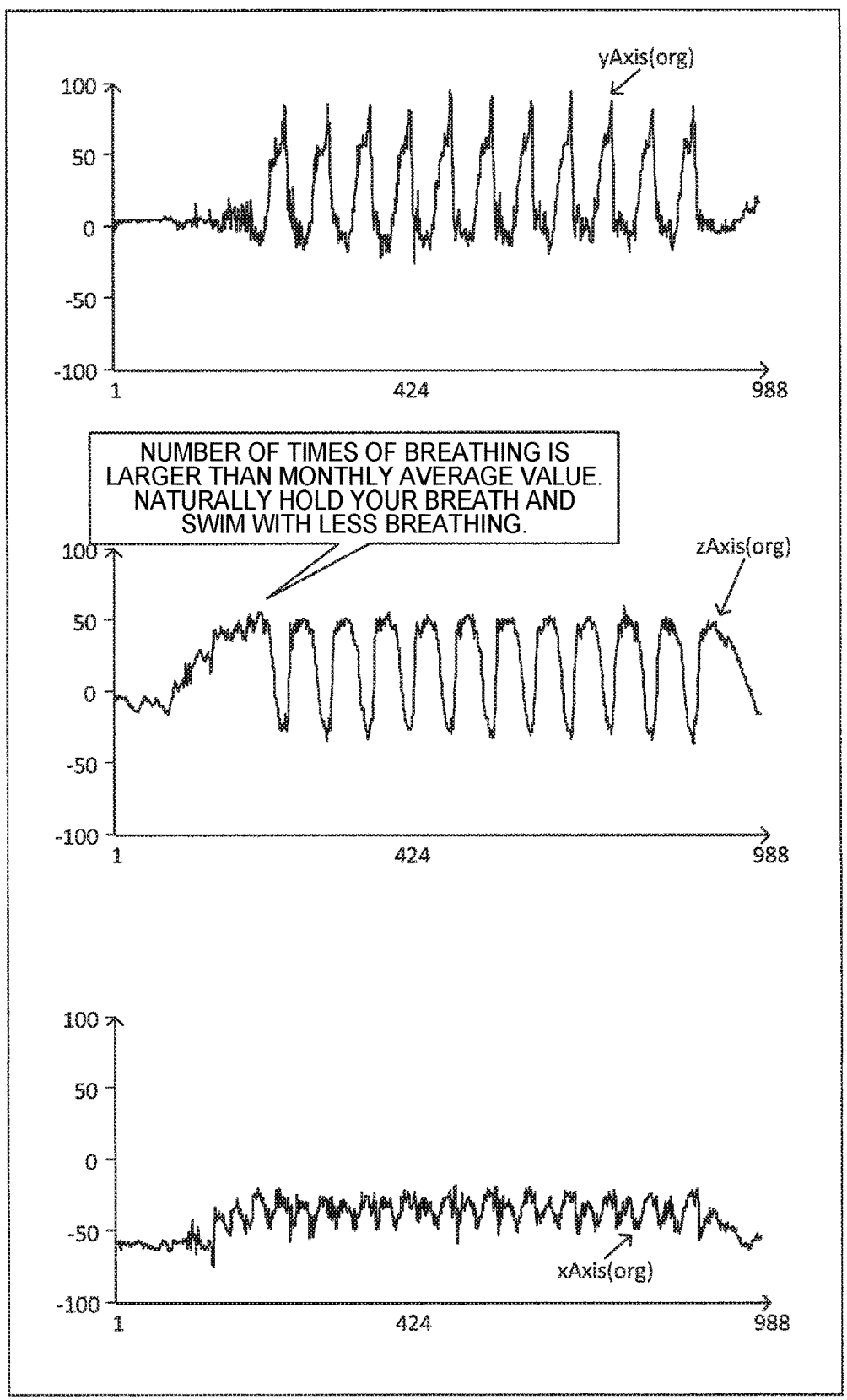
FIG. 22 illustrates an example (in a case of using the head acceleration sensor) of a screen displaying advice along with a sensor output graph.

For example, the processor 120 of the electronic apparatus 1 accesses the server 4 via the information terminal 2, and refers to data regarding the past number of times of breathing regarding a user of the electronic apparatus 1. The processor 120 compares an average value of the past number of times of breathing with the present number of times of breathing, and displays advice that the number of times of breathing is to be reduced on the display 170 in a case where the present number of times of breathing is larger than the average value. FIG. 22 illustrates an example (in a case of using the head acceleration sensor) of a screen displaying advice along with a sensor output graph (a graph of acceleration data). In this example, a text image with the content that "the number of times of breathing is larger than the monthly average value; and try to naturally hold your breath and swim with less breathing" is displayed as advice.

It is assumed that information regarding a distance which a user has swum or a swimming stroke which has been employed by the user is added to each piece of measured data stored in the server 4, and measured data (herein, data regarding the number of times of breathing) used as a comparison target by the processor 120 is limited to data in the same swimming stroke and the same distance as the present measured data (herein, data regarding the number of times of breathing).

1-5-2. Advice on Stroke Time (Third Example)

The processor 120 of the electronic apparatus 1 may give the user, for example, advice on stroke time in the left-right-balance display process using the waist acceleration sensor (Third Example).

For example, if average right stroke time and average left stroke time are calculated on the basis of timings or the like of a peak and a valley generated in a predetermined component of stroke data, the processor 120 of the electronic apparatus 1 may compare the average right stroke time with the average left stroke time, display advice that the right stroke time is to be increased on the display 170 in a case where the average right stroke time is shorter than the average left stroke time, and display advice that the left stroke time is to be increased on the display 170 in a case where the average left stroke time is shorter than the average right stroke time.

Figure 23:
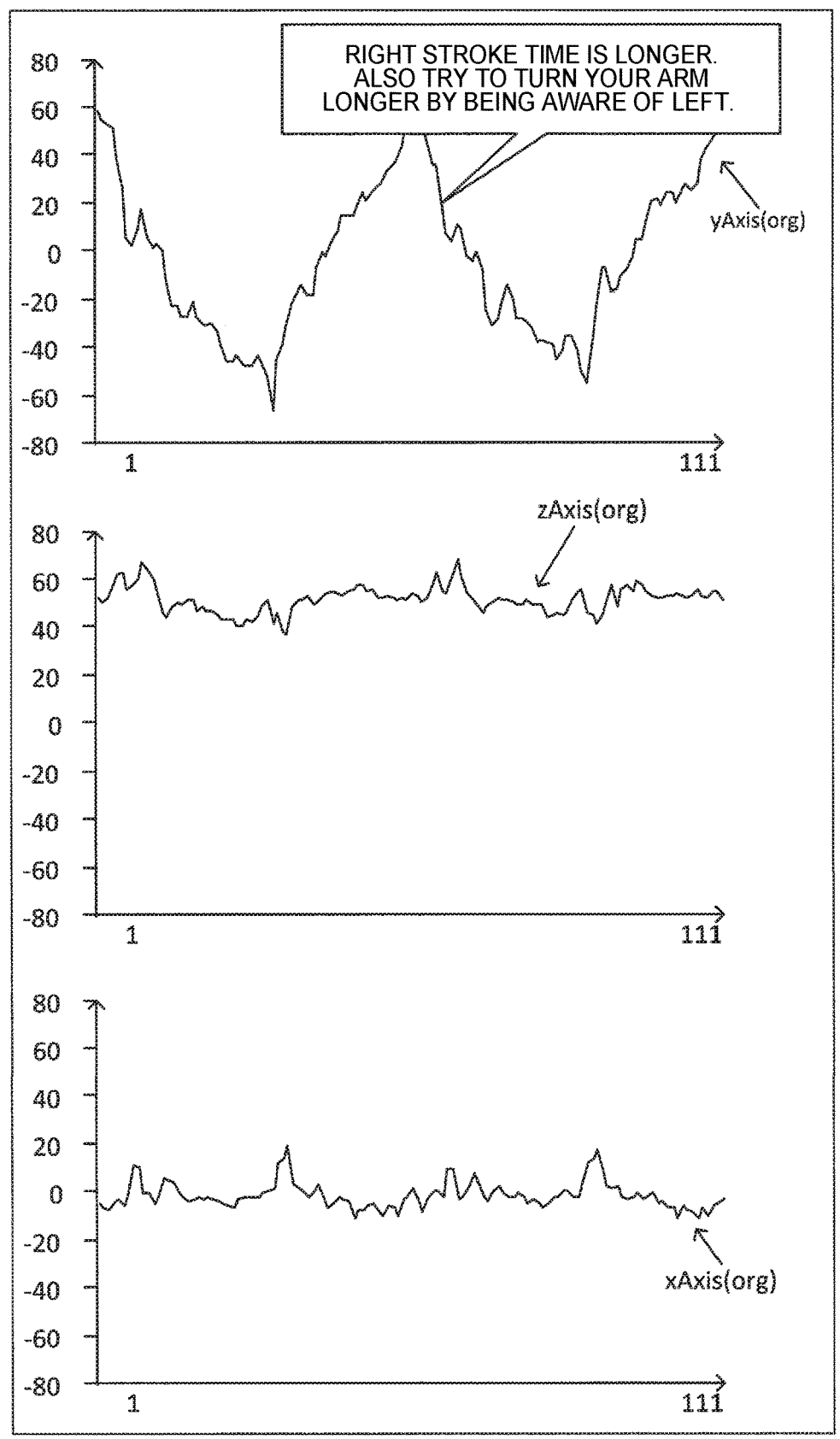
FIG. 23 illustrates an example (in a case of using the waist acceleration sensor) of a screen displaying advice along with a sensor output graph.

FIG. 23 illustrates an example (in a case of using the waist acceleration sensor) of a screen displaying advice along with a sensor output graph. In this example, a text image with the content that "the right stroke time is longer; and also try to turn your arm longer by being aware of the left" is displayed as advice.

Herein, a description has been made of advice in the third Example, but the same advice may also be given in other Examples.

1-5-3. Advice on Driving Force (Third Example)

The processor 120 of the electronic apparatus 1 may give the user, for example, advice on driving force in the left-right-balance display process using the waist acceleration sensor (third Example).

For example, if average right stroke driving force and average left stroke driving force are calculated, the processor 120 of the electronic apparatus 1 may compare the average right stroke driving force with the average left stroke driving force, display advice that the right stroke driving force is to be increased on the display 170 in a case where the average right stroke driving force is lower than the average left stroke driving force, and display advice that the left stroke force is to be increased on the display 170 in a case where the average left stroke driving force is lower than the average right stroke driving force.

Figure 24:
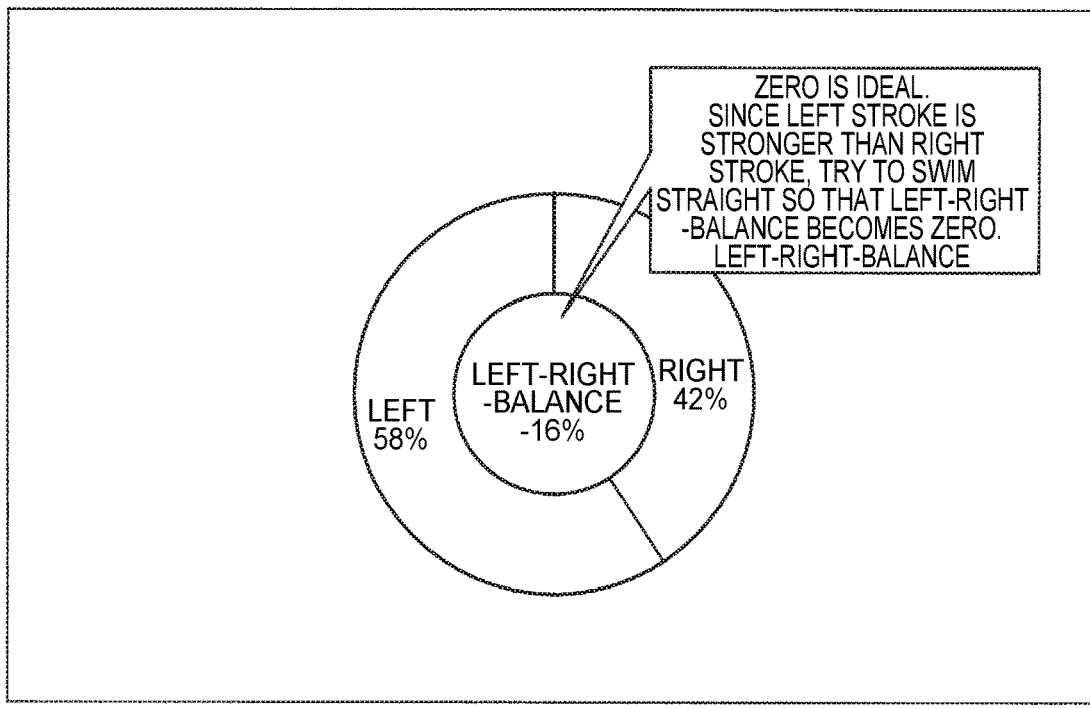
FIG. 24 illustrates an example (in a case of using the waist acceleration sensor) of a screen displaying advice along with a pie chart.

FIG. 24 illustrates an example (in a case of using the waist acceleration sensor) of a screen displaying advice along with a pie chart. In this example, a text image with the content that "zero is ideal; since the left stroke is stronger than the right stroke, try to swim straight so that left-right-balance becomes zero" is displayed as advice.

Herein, a description has been made of advice in the third Example, but the same advice may also be given in other Examples.

1-5-4. Advice on Bending Degree (Third Example)

The processor 120 of the electronic apparatus 1 may give the user, for example, advice on a bending degree in the left-right-balance display process using the waist acceleration sensor (third Example).

Figure 25:
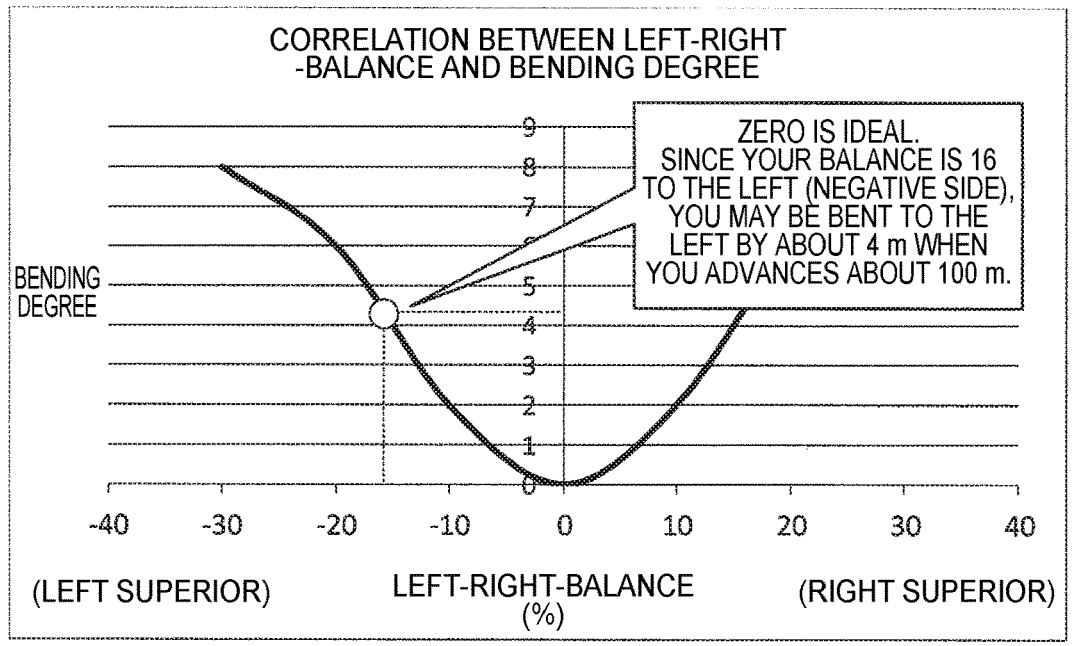
FIG. 25 illustrates an example (in a case of using the waist acceleration sensor) of a screen displaying advice along with a correlation graph.

For example, if a bending degree is calculated on the basis of the above-described left-right-balance $\Delta$, the processor 120 of the electronic apparatus 1 may display advice required for the user to advance straight on the display 170. FIG. 25 illustrates an example (in a case of using the waist acceleration sensor) of a screen displaying advice along with a correlation graph. In this example, a text image with the content that "zero is ideal; and, since your balance is 16 to the left (negative side), you may be bent to the left by about 4 m when you advance about 100 m" is displayed as advice.

1-5-5. Advice on Rolling (Fourth Example)

The processor 120 of the electronic apparatus 1 may give the user, for example, advice on rolling in the left-right-balance display process based on rolling (fourth Example).

For example, the processor 120 of the electronic apparatus 1 may calculates ratio (or a difference) between time for which the body is rolling to the right arm side and time for which the body is rolling to the left arm side, display advice that the time for which the body is rolling to the left arm side is to be increased on the display 170 in a case where the time for which the body is rolling to the left arm side is shorter than the time for which the body is rolling to the right arm side, and display advice that the time for which the body is rolling to the right arm side is to be increased on the display 170 in a case where the time for which the body is rolling to the right arm side is shorter than the time for which the body is rolling to the left arm side.

Figure 26:
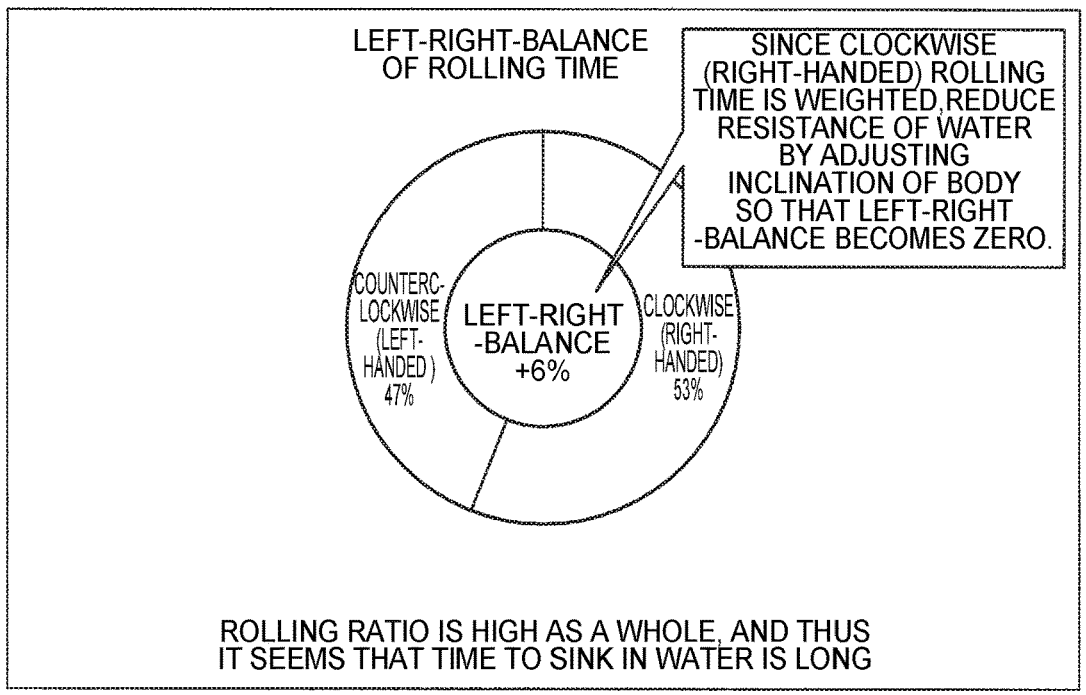
FIG. 26 illustrates an example (in a case of using a rolling time) of a screen displaying advice along with a pie chart.

FIG. 26 illustrates an example (in a case of using rolling time) of a screen displaying advice along with a pie chart. In this example, a text image with the content that "since clockwise (right-handed) rolling time is weighted, reduce resistance of water by adjusting an inclination of the body so that left-right-balance becomes zero" is displayed as advice.

1-5-6. Advice on Flutter Kick (Fifth Example)

The processor 120 of the electronic apparatus 1 may give the user, for example, advice on flutter kick in the left-right-balance display process regarding flutter kick (fifth Example).

For example, if average right stroke driving force and average left stroke driving force are calculated, the processor 120 of the electronic apparatus 1 may compare the average right stroke driving force with the average left stroke driving force, display advice that the right stroke driving force is to be increased on the display 170 in a case where the average right stroke driving force is lower than the average left stroke driving force, and display advice that the left stroke driving force is to be increased on the display 170 in a case where the average left stroke driving force is lower than the average right stroke driving force.

Figure 27:
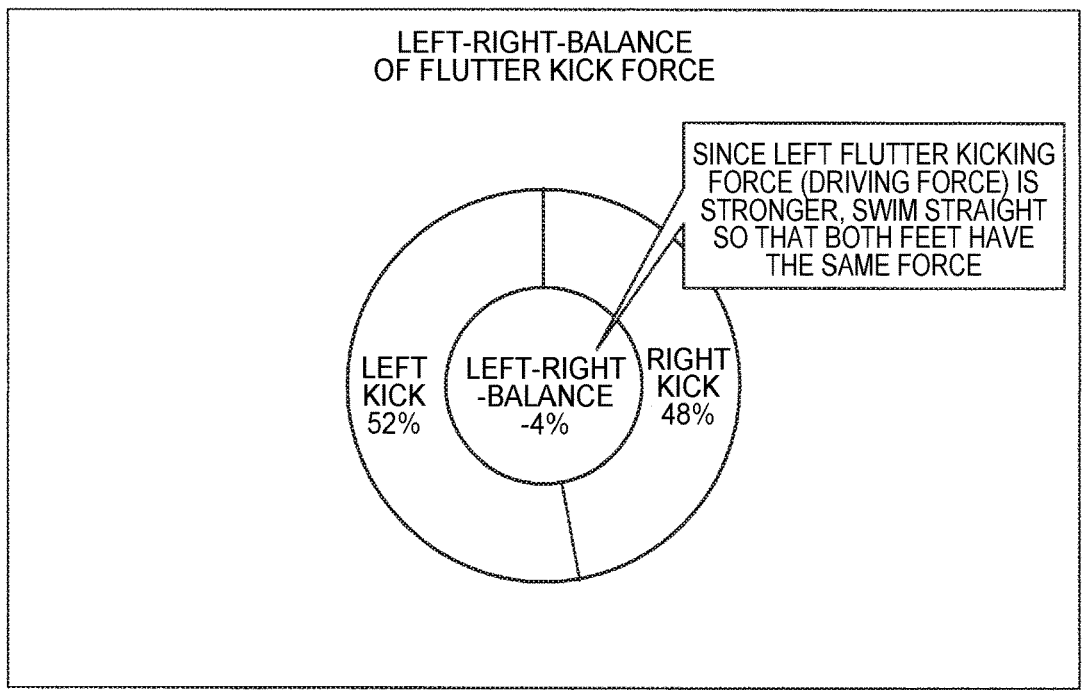
FIG. 27 illustrates an example (in a case of measuring flutter kicks) of a screen displaying advice along with a pie chart.

FIG. 27 illustrates an example (in a case of performing flutter kick) of a screen displaying advice along with a pie chart. In this example, a text image with the content that "since left flutter kicking force (driving force) is stronger, swim straight so that both feet have the same force" is displayed as advice.

1-6. Operations and Effects of Embodiment

As described above, in the system of the present embodiment, the processor 120 of the electronic apparatus 1 outputs information regarding a left-right difference (balance) of strokes in swimming on the basis of data which is output from a sensor mounted on the body of a user during swimming, and the display 170 of the electronic apparatus 1 displays the information regarding a left-right difference (balance) which is output from the processor 120.

Since information output from the processor 120 and information displayed on the display 170 change depending on cases where at least left-right-balance of swimming forms of a user is favorable and unfavorable, the user can check the quality of at least the left-right-balance of the swimming forms thereof on the basis of the information. The left-right-balance is an important element among the swimming forms, and thus the information is effective information for easily and reliably improving the swimming forms.

2. Modification Example 2-1. Variation of System Configuration

If the system of the present embodiment includes a portable apparatus having a sensor which can be mounted on a user's body, any one of the electronic apparatus 1, the sensor device 1C, the information terminal 2, and the server 4 may be omitted.

Sharing of functions in the system is not limited to the above description.

For example, some or all of the functions of the sensor device 1C may be installed in the electronic apparatus 1, and may be installed in the information terminal 2.

Some or all of the functions of the electronic apparatus 1 may be installed in the sensor device 1C, and may be installed in the information terminal 2.

Some or all of the functions of the information terminal 2 may be installed in the sensor device 1C, and may be installed in the electronic apparatus 1.

Some of the functions of the information terminal 2 may be installed in the server 4, and some of the functions of the server 4 may be installed in the information terminal 2.

2-2. Variation of Sensor

The sensor device 1C or the electronic apparatus 1 of the embodiment may use at least one of the following various sensors as a sensor. In other words, the various sensors are, for example, an acceleration sensor, a GPS (GNSS) sensor, an angular velocity sensor, a speed sensor, a heartbeat sensor (a chest belt or the like), a pulse sensor (a sensor performing measurement at locations other than the heart), a pedometer, a pressure sensor, an altitude sensor, a temperature sensor (an atmospheric temperature sensor or a body temperature sensor), a geomagnetic sensor, a weight meter (which is used as an external device of the system), an ultraviolet sensor, a perspiration sensor, a blood pressure sensor, a blood oxygen concentration ($SpO_2$) sensor, a lactic acid sensor, a blood sugar level sensor, and a wind speed sensor. A sensor which is not used for measurement may not be mounted in the apparatus in the embodiment.

2-3. Notification Aspects

At least one of the electronic apparatus 1, the sensor device 1C, or the information terminal 2 may perform a notification of information for a user through image display, may perform a notification not only through image display but also through sound output or by using vibration, light, or a color (light emission from an LED or a display color of a display), and may perform a notification through a combination of at least two of image display, sound output, vibration, light, and a color.

2-4. Customizing

At least some of the notification content (including a notification period, a notification item, a notification aspect, a collecting method, a notification order, and the like) for a user in the electronic apparatus 1, the sensor device 1C, and the information terminal 2 of the embodiment may be set in advance by the user (customizable).

2-5. Forms of Apparatus

The electronic apparatus 1 may be configured as portable information terminals of various types, such as a wrist type electronic apparatus, an earphone type electronic apparatus, a ring type electronic apparatus, a pendant type electronic apparatus, an electronic apparatus attached to a sport appliance and used, a smartphone, a head mounted display (HMD), and a head up display (HUD).

2-6. Comparison with Other Users

In the present system, a curve related to a temporal change in a depth of a stroke in swimming for a certain user may be output to overlap a curve related to a temporal change in a depth of a stroke in swimming for another user who is different from the user. For example, another user may be an expert, a coach, or an athlete. This case can be used to improve a form or skill of the user.

2-7. Determination of Swimming Stroke

In the present system, a swimming stroke may be determined on the basis of the curve related to a temporal change in a depth of a stroke in swimming (on the basis of a shape of the curve, a depth, and the like), and the determined result (swimming stroke) may be output. In this case, since the output information is correlated with a swimming stroke (the crawl, the butterfly, the backstroke, the breaststroke, and the like), a user can look back on the swimming stroke by using the information as a practice diary, and thus the information can be used to improve a swimming form of the user.

2-8. Applications

A coach may have a separate apparatus in addition to a swimmer, and wireless communication may be performed between the apparatuses in real time so that a stroke trajectory is specified in order to coach the swimmer.

Sensor devices may be mounted on both of the left and right hands, and stroke trajectories of both hands may be specified. A sensor device may be mounted on the leg, and the strength of flutter kick or dolphin kick may be specified.

The present system may be used to specify an arm trajectory in dividing, land sports other than swimming, ball games, and the like.

2-8. Optional Functions

Other functions may be installed in at least one of the sensor device 1C, the electronic apparatus 1, and the information terminal 2. Other functions may be, for example, well-known smartphone functions. The smartphone functions include, for example, a call function, a mail incoming notification function, a call incoming notification function, a communication function, and a camera function.

2-9. Positioning System

In the embodiment, as a satellite positioning system, a global positioning system (GPS) is used, but a global navigation satellite system (GNSS) may be used. For example, one or two or more of satellite positioning systems such as a European Geostationary-Satellite Navigation Overlay Service (EGNOS), a quasi zenith satellite system (QZSS), a global navigation satellite system (GLONASS), GALILEO, a BeiDou navigation satellite system (BeiDou) may be used. As at least one of the satellite positioning systems, a satellite-based augmentation system (SBAS) such as European geostationary-satellite navigation overlay service (EGNOS) or a wide area augmentation system (WARS) may be used.

3. Others

The invention is not limited to the above-described embodiment, and may be variously modified within the scope of the spirit of the invention.

The above-described embodiment and modification examples are only examples, and the invention is not limited thereto. For example, the embodiment and the respective modification examples may be combined with each other as appropriate.

The invention includes substantially the same configuration (for example, a configuration in which functions, methods, and results are the same, or a configuration in which objects and effects are the same) as the configuration described in the embodiment. The invention includes a configuration in which an inessential part of the configuration described in the embodiment is replaced with another part. The invention includes a configuration which achieves the same operation and effect or a configuration capable of achieving the same object as in the configuration described in the embodiment. The invention includes a configuration in which a well-known technique is added to the configuration described in the embodiment.

What is claimed is:

1. An electronic apparatus comprising:
a communicator that obtains sensor data output from a sensor mounted on a body of a swimmer; and
a processor programmed to output information regarding a left-right difference between a left stroke and a right stroke during swimming, the information being based on the sensor data,
wherein the information regarding the left-right difference includes a deviation between a curve related to a temporal change in a depth of the right stroke and a curve related to a temporal change in a depth of the left stroke.

2. The electronic apparatus according to claim 1, wherein the information regarding the left-right difference includes a difference between a time required for the right stroke and a time required for the left stroke.

3. The electronic apparatus according to claim 1, wherein the information regarding the left-right difference includes a difference between driving force based on the right stroke and driving force based on the left stroke.

4. The electronic apparatus according to claim 1,
wherein the processor is programmed to calculate deviation relative to a predetermined straight advancing direction due to a difference between driving force based on the right stroke and driving force based on the left stroke, and
the information regarding the left-right difference includes an extent of the calculated deviation.

5. The electronic apparatus according to claim 1, wherein the information regarding the left-right difference includes a difference between time for which the body is rolling to a right arm side and time for which the body is rolling to a left arm side, with an advancing direction in the swimming as a rotation axis.

6. The electronic apparatus according to claim 1, wherein the sensor includes at least one of an atmospheric pressure sensor, an acceleration sensor, and an angular velocity sensor.

7. A system comprising:
the electronic apparatus according to claim 1; and
the sensor.

8. The electronic apparatus according to claim 1, wherein the information includes advice.

9. The electronic apparatus according to claim 1, wherein the processor is programmed to output a curve related to a temporal change in a depth of a stroke in the swimming and a curve related to a temporal change in a depth of a stroke in the swimming of another user, who is different from the swimmer, in an overlapping manner.

10. The electronic apparatus according to claim 1, wherein the processor is programmed to:
determine a swimming stroke based on a curve related to a temporal change in a depth of the swimming stroke; and
output a result of the determination.

11. An electronic apparatus comprising:
a processor programmed to output information regarding a left-right difference between a left stroke and a right stroke of a swimmer during swimming, the information being based on sensor data output from a sensor mounted on a body of the swimmer; and
a display that displays the information regarding the left-right difference,
wherein the information regarding the left-right difference includes a deviation between a curve related to a temporal change in a depth of the right stroke and a curve related to a temporal change in a depth of the left stroke.

12. The electronic apparatus according to claim 11, wherein the information regarding the left-right difference includes a graph in which the curve related to the temporal change in the depth of the right stroke overlaps the curve related to the temporal change in the depth of the left stroke.

13. The electronic apparatus according to claim 11, wherein the information regarding the left-right difference includes a graph indicating a difference between a time required for the right stroke and a time required for the left stroke.

14. The electronic apparatus according to claim 11, wherein the information regarding the left-right difference includes a graph indicating a difference between driving force based on the right stroke and driving force based on the left stroke.

15. The electronic apparatus according to claim 11, wherein the information regarding the left-right difference includes a graph indicating deviation relative to a predetermined straight advancing direction due to a difference between driving force based on the right stroke and driving force based on the left stroke.

16. The electronic apparatus according to claim 11, wherein the information regarding the left-right difference includes a graph indicating a difference between time for which the body is rolling to a right arm side and time for which the body is rolling to a left arm side, with an advancing direction in the swimming as a rotation axis.

17. A control method comprising:
performing control so that information regarding a left-right difference between a left stroke and a right stroke during swimming is output or displayed based on data which is output from a sensor mounted on a body of a swimmer,
wherein the information regarding the left-right difference includes a deviation between a curve related to a temporal change in a depth of the right stroke and a curve related to a temporal change in a depth of the left stroke.

18. A non-transitory storage medium containing program instructions that when executed by a processor, cause the processor to:
obtain sensor data output from a sensor mounted on a body of a swimmer; and
output or display information regarding a left-right difference between a left stroke and a right stroke during swimming, the information being based on the sensor data,
wherein the information regarding the left-right difference includes a deviation between a curve related to a temporal change in a depth of the right stroke and a curve related to a temporal change in a depth of the left stroke.

19. An electronic apparatus mounted to a body of a swimmer for obtaining motion data and displaying information based on the motion data to the swimmer, comprising:
a sensor that obtains the motion data during swimming;
a processor programmed to:
identify a left stroke and a right stroke based on the sensor data during swimming;
determine characteristics of the left stroke and the right stroke based on the sensor data; and
output information regarding a left-right difference between the left stroke and the right stroke; and
a display that displays the information,
wherein the information regarding the left-right difference includes a deviation between a curve related to a temporal change in a depth of the right stroke and a curve related to a temporal change in a depth of the left stroke.

* * * * *